US006552167B1

(12) United States Patent
Rose

(10) Patent No.: US 6,552,167 B1
(45) Date of Patent: Apr. 22, 2003

(54) POLYAMIDE CHAINS OF PRECISE LENGTH

(75) Inventor: Keith Rose, Geneva (CH)

(73) Assignee: Gryphon Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/379,297

(22) Filed: Aug. 23, 1999

Related U.S. Application Data

(60) Provisional application No. 60/124,266, filed on Mar. 11, 1999, provisional application No. 60/105,261, filed on Oct. 22, 1998, and provisional application No. 60/098,351, filed on Aug. 28, 1998.

(51) Int. Cl.[7] .......................... C07K 1/07; C08G 69/10
(52) U.S. Cl. ..................... 530/326; 525/420; 528/335; 530/327; 530/328; 530/345; 530/409
(58) Field of Search ..................... 562/561; 564/160; 528/335; 525/50.42, 432; 530/326, 327, 328, 345, 405, 409, 188; 435/188; 424/179.1, 180.1, 181.1, 194.1, 94.3

(56) References Cited

U.S. PATENT DOCUMENTS

| | | | |
|---|---|---|---|
| 3,788,948 A | | 1/1974 | Kagedal et al. ............. 435/180 |
| 3,960,830 A | | 6/1976 | Bayer et al. ................ 530/334 |
| 4,002,531 A | | 1/1977 | Royer et al. ................ 435/188 |
| 4,028,313 A | * | 6/1977 | Bodanszky et al. ........... 528/69 |
| 4,055,635 A | | 10/1977 | Green et al. ................ 424/400 |
| 4,179,337 A | | 12/1979 | Davis et al. ................ 435/181 |
| 4,192,798 A | * | 3/1980 | Verlander et al. ........... 530/334 |
| 4,261,973 A | | 4/1981 | Lee et al. ................... 424/78.3 |
| 4,412,989 A | | 11/1983 | Iwashita et al. ............. 514/762 |
| 4,414,147 A | | 11/1983 | Klibanov et al. ............ 530/351 |
| 4,415,665 A | | 11/1983 | Mosbach et al. ............ 435/179 |
| 4,609,546 A | | 9/1986 | Hiratani ........................ 514/2 |
| 4,732,863 A | | 3/1988 | Tomasi et al. .............. 436/547 |
| 4,732,890 A | * | 3/1988 | Bonelli et al. ................ 514/11 |
| 4,745,180 A | | 5/1988 | Moreland et al. ........... 530/351 |
| 4,824,659 A | * | 4/1989 | Hawthorne .................... 424/1.1 |
| 5,097,070 A | * | 3/1992 | Lin et al. .................... 564/153 |
| 5,122,614 A | | 6/1992 | Zalipski ...................... 548/520 |
| 5,476,870 A | * | 12/1995 | Renaut et al. .............. 514/482 |
| 5,556,948 A | | 9/1996 | Tagawa et al. .......... 530/391.9 |
| 5,672,662 A | | 9/1997 | Harris et al. ................ 525/408 |
| 5,739,208 A | | 4/1998 | Harris ........................ 525/54.1 |
| 5,777,096 A | | 7/1998 | Grossman et al. ......... 536/24.3 |
| 6,294,697 B1 | | 9/2001 | Wilbur et al. ............... 564/505 |

FOREIGN PATENT DOCUMENTS

| | | | |
|---|---|---|---|
| EP | 0 098 110 | 1/1984 | |
| EP | 0 152 847 | 8/1985 | |
| EP | 0 234 929 | 11/1987 | |
| EP | 0 605 963 | 7/1994 | |
| JP | 57-92435 | 6/1982 | |
| WO | WO 94/12220 | 6/1994 | |
| WO | WO 95/17886 | 6/1995 | |
| WO | WO 97/14740 | 4/1997 | ........... C08G/65/32 |

OTHER PUBLICATIONS

Rose et al. Stepwise Solid–Phase Synthesis of Polyamides . . . J. Am. Chem. Soc. vol. 121, pp. 7034–7038, Aug. 4, 1999.*
Abuhowski et al., "Alteration of Immunological Properties of Bovine Serum Albumin by Covalent Attachment of Polyethylene Glycol," J. Biol. Chem., 252(11) :3578–3581 (1977).
Bethell et al., "A Novel Method of Activation of Cross–Linked Agaroses with 1,1'–Carbonyldiimidazole Which Gives a Matrix for Affinity Chromatography Devoid of Additional Charged Groups," J. Biol. Chem., 254(8) :2572–2574 (1979).
Bettinger et al., "Conventional Polymer–Supported Synthetic Route to Heterobifunctional Polyethylene Glycols," Bioconjugate Chem., 9:842–846 (1998).
Ferrari et al., "ExGen 500 is an Efficient Vector for Gene Delivery to Lung Epithelial Cells in Vitro and in Vivo," Gene Therapy, 4:1100–1106 (1997).
Hai et al., "Synthesis of Water–Soluble, Nonimmunogenic Polyamide Cross–Linking Agents," Bioconjugate Chem., 9 : 645–654–654 (1998).
Johnson et al., "Amino–Terminal Dimerization of an Erythropoietin Mimetic Peptide Results in Increased Erythropoietic Activity," Chemistry and Biology, 4(12) :939–950 (1997).
Johnson et al., "Heterobifunctional Cross–Linkers Containing 4,9–Dioxa–1,12–dodecanediamine Spacers," Bioconjugate Chem., 8 :447–452 (1997).
Kramer et al., "Spanning Binding Sites on Allosteric Proteins with Polymer–Linked Ligand Dimers," Nature, 395:710–713 (1998).
Lu et al., "Pegulated Peptides II: Solid–Phase Synthesis of Amino–, Carboxy– and Side–Chain Pegylated Peptides," Int. J. Peptide Protein Res., 43 :127–138 (1994).
Peters et al., "Molecular Barbells," Science, 282:1439 (1998).
Rose et al., "Facile Synthesis of Homogeneous Artificial Proteins," J. Am. Chem. Soc., 116:30–33 (1994).
Rose et al., "Natural Peptides as Building Blocks for the Synthesis of Large Protein–like Molecules with Hydrazone and Oxime Linkages," Bioconjugate Chem., 7:552–556 (1996).
Terskikii et al., "Peptabody: A New Type of High Avidity Binding Protein," Proc. Natl. Acad. Sci. USA, 94(5):1663–1668 (1997).

(List continued on next page.)

Primary Examiner—Jeffrey E. Russel
(74) Attorney, Agent, or Firm—Jeffrey I. Auerbach; Liniak, Berenato & White, LLC

(57) ABSTRACT

Provided are chains of precise length and methods for their preparation. These chains are formed by the reaction of a derivative of a diacid and a diamine in a stepwise manner on a support. One of the reactants contains a water soluble oligomer, preferably polyethylene glycol. These chains are then used to chemically modify target macromolecules such as biologically important polypeptides.

68 Claims, No Drawings

OTHER PUBLICATIONS

Tsutsumi et al., "Chemical Modification of Natural Human Tumor Necrosis Factor– with Polyethylene Glycol Increases Its Anti–tumor Potency," Jpn. J. Cancer Res., 85:9–12 (1994).

Vilaseca et al., "Protein Conjugates of Defined Structure: Synthesis of Use of a New Carrier Molecule," Am. Chem. Soc., Bioconjugate Chem., 4(6) :515–520 (1993).

Werlen et al., "Preparation of a Trivalent Antigen–Binding Construct Using Polyoxime Chemistry: Improved Biodistribution and Potential for Therapeutic Application," Can. Res., 56:809–815 (1996).

Wilbur et al., "Biotin Reagents for Antibody Pretargeting. Synthesis, Radioiodination, and in Vitro Evaluation of Water Soluble, Biotinidase Resistant Biotin Derivatives," Bioconjugate Chem., 8:572–584 (1997).

Zalipsky, "Functionalized Poly(ethylene Glycol) for Preparation of Biologically Relevant Conjugates," Bioconjugate Chem., 6:150–165 (1995).

Bertozzi, C.R. et al., "The Synthesis of Heterobifunctional Linkers for the Conjugation of Ligands to Molecular Probes," J. Org. Chem. 56:4329–4333 (1991).

Caldwell, G. et al., "Water Soluble Polyamides as Potential Drug Carriers. IX. Polyaspartamides Grafted with Amine-Terminated Poly (Ethylene Oxide) Chains," Journal of Applied Polymer Science, 66:911–919 (1997).

Cook, R.M. et al., "The Preparation and Synthetic Application of Heterobifunctional Biocompatible Spacer Arms," Tetrahedron Lett. 35(37):6777–6780 (1994).

Coudert, G. et al., "A Novel Unequivocal Synthesis of Polyethylene Glycols," Synthetic Comm. 16(1):19–26 (1986).

Johnson, G.M. et al., "Heterobifunctional Cross–Linkers Containing 4,9–Dioxa–1,12–dodecanediamine Spacers," Bioconjugate Chem. 8:447–452 (1997).

Keegstra, E.M.D. et al., "A Highly Selective Synthesis of Monodisperse Oligo(ethylene glycols)," J. Org. Chem. 57:6678–6680 (1992).

Kinugasa, S. et al., "Preparation and Characterization of Pure Oligo(ethylene glycol)s. 2," Macromolecules 25:4848–4853 (1992).

Lane, J.W., et al., "Sensitive Detection of Catalytic Species without Chromophoric Substrates," J. Amer. Chem. Soc. 115:2078–2080 (1993).

Nakatsuji, Y. et al., "A Facile Synthesis of Hexa–and Octa-ethylene Glycols" Synthesis, Communications, pp. 280–281 (1987).

Nielsen, J. et al., "Synthetic Methods for the Implementation of Encoded Combinatorial Chemistry," J. Amer. Chem. Soc. 115:9812–9813 (1993).

Ogata, N. et al., "Active Polycondensation of Dicarboxylic Acid Derivatives Having β–Hetero Arms," Polymer J. 5(2):186–194 (1973).

Pathare, P.M. et al., "Synthesis of Cobalamin Dimers Using Isophthalate Cross–Linking of Corrin Ring Carboxylates and Evaluation of their Binding to Transcobalamin II," Bioconjugate Chem. 8:161–172 (1997).

Peppel, W.J., "Water–Soluble Polyamides," J. Polymer Sci. 51(156):S64–S66 (1961).

Redeuilh, G. et al., "The Use of the Biotinyl Estradiol–Avidin System for the Purification of "Nontransformed" Estrogen Receptor by Biohormonal Affinity Chromatography," J. Biol. Chem. 260(7):3996–4002 (1985).

Sato, H. et al., "Preparation of Regularly Sequenced Polyamides, Containing Definite Numbers of Oxyethylene Units," Makromol. Chem. 182:755–762 (1981).

Wilbur, D.S. et al., "Biotin Reagents for Antibody Pretargeting. Synthesis, Radioiodination, and in Vitro Evaluation of Water Soluble, Biotinidase Resistant Biotin Derivatives," Bioconjugate Chem. 8:572–584 (1997).

Wilbur, D.S. et al., "Biotin Reagents for Antibody Pretargeting. 4. Selection of Biotin Conjugates for in Vivo Application Based on Their Dissociation Rate from Avidin and Streptavidin," Bioconjugate Chem. 11:569–583 (2000).

Wilbur, D.S. et al., "Evaluation of Biotin–Dye Conjugates for Use in an HPLC Assay To Assess Relative Binding of Biotin Derivatives with Avidin and Streptavidin," Bioconjugate Chem. 11:584–598 (2000).

Wilbur, D.S. et al., "Biotin Reagents for Anitbody Pretargeting. 5. Additional Studies of Biotin Conjugate Design To Provide Biotinidase Stability," Bioconjugate Chem. 12:616–623 (2001).

* cited by examiner

POLYAMIDE CHAINS OF PRECISE LENGTH

CROSS-REFERENCE TO RELATED APPLICATIONS

This Application Claims priority to U.S. Provisional Application No. 60/124,266, filed Mar. 11, 1999, U.S. Provisional Application No. 60/105,261, filed Oct. 22, 1998, and U.S. Provisional Application No. 60/098,351, filed Aug. 28, 1998.

TECHNICAL FIELD

The present invention relates to polyamide chains of precise length (i.e., a precise number of monomer units) and methods for their preparation. More particularly, the present invention relates to methods for chemically modifying target molecules, e.g. macromolecules, particularly biologically important polypeptides, and surfaces (e.g., gold or glass) by means of covalent attachment of polyamide chains of precise length. Even more particularly, the invention relates to polyethylene glycol-based chains of precise length.

BACKGROUND

It is well recognized that the properties of numerous materials such as peptides, polypeptides such as proteins, and bioconjugates, can be enhanced by grafting organic chain-like molecules onto them. Such grafting can increase the usefulness of a material as a linker to connect multiple copies of a structural motif, increase a material's shielding from the immune system, and increase the half-life of a material. Biosensor surfaces may also be enhanced by first grafting organic chain-like molecules onto the surface (usually gold or glass) prior to covalent attachment of biomolecules, for example, the dextran coated sensors sold by Biacore AB (Sweden).

The organic chain-like molecules often used to enhance properties are polyethylene glycol-based or "PEG-based" chains, i.e., chains that are based on the repeating unit —$CH_2CH_2O$—. See for example, Tsutsumi, et al., *Jpn. J Cancer Res.* 85:9–12 (1994), where an ester of monomethoxy polyethylene glycol was shown to increase the potency of human tumor necrosis factor-α. PEG-based chains are flexible, amphiphilic, non-immunogenic and not susceptible to cleavage by proteolytic enzymes. Preparations of materials that have been modified by PEG or PEG-based chains, have reduced immunogenicity and antigenicity. See for example, Abuchowski, et al., *Journal of Biological Chemistry* 252(11):3578–3581 (1977), where PEG was shown to alter the immunological properties of bovine serum albumin. PEG also serves to increase the molecular size of the material to which it is attached, thereby increasing its biological half-life. These beneficial properties of the PEG-modified materials make them very useful in a variety of therapeutic applications.

The grafting of PEG chains or PEG-based chains onto proteins is known. See for example, Zalipsky, U.S. Pat. No. 5,122,614, which describes PEG that is converted into its N-succinimide carbonate derivative. Also known are PEG chains modified with reactive groups to facilitate grafting onto proteins. See for example, Harris, U.S. Pat. No. 5,739,208, which describes a PEG derivative that is activated with a sulfone moiety for selective attachment to thiol moieties on molecules and surfaces and Harris, et al., U.S. Pat. No. 5,672,662, which discloses active esters of PEG acids that have a single propionic or butanoic acid moiety. This area is extensively reviewed in Zalipsky, *Bioconjugate Chemistry* 6:150–165 (1995). Besides use of PEG, Wright, EP 0 605 963 A2 describes linking reagents that contain water soluble polymers that form a hydrazone linkage with an aldehyde group on a protein.

Polyamide chains also are useful as organic chain-like molecules to enhance properties. In addition, acute toxicity screening in rodents suggests that polyamides are neither toxic nor immunogenic (Hai, et al., *Bioconj. Chem.* 9:645–654 (1998)).

Problems are encountered, however, since state of the art technology does not provide for the synthesis of organic chain-like molecules having a determinable length.

Techniques used to prepare PEG or PEG-based chains, even those of fairly low molecular weight such as 3400 (see for example, Kramer, et al., *Nature* 395:710 (1998)), involve a poorly-controlled polymerization step which leads to preparations having a spread of chain lengths about a mean value, i.e., they involve polymer preparations of —$(CH_2CH_2O)_m$— where m does not have a discrete value but rather, has a range of values about a mean. This is very evident in mass spectra of PEG chains themselves and of compounds to which PEG chains have been grafted. For example, in Johnson, et al., *Chemistry & Biology* 4:939 (1997), PEG chains of nominal relative molecular mass 3400 and 5000, when grafted onto a small peptide, give rise to products with mass ranges of mean ±1000, i.e., a range of 2000 amu. This is a typical result of state of the art methods. When sufficient mass resolution is available, the spectrum shows many signals spaced 44 amu apart. See, for example, Lu, et al., *Int. J. Peptide Protein Res.* 43:127–138 (1994). This large range in mass corresponds to a corresponding range in chain lengths. Accordingly, products containing such PEG or PEG-based chains are not homogeneous and consist of molecules possessing short, medium and long chains. The situation is worse for compounds possessing two PEG chains as, statistically, they must consist of a mixture of molecules possessing two short chains, a short and a long chain, and two long chains, so the variance in mass is larger than for products which have only one chain. Since chain length affects mass, biological half-life, shielding from the immune system, and spacing of subunits when such a chain is used to link two moieties (as in Johnson, et al., Chemistry & Biology, supra), the biological effect of a compound which possesses one or more conventional PEG chains is that of an average of the effects of the individual species present (those with short chains, those with medium chains and those with long chains) and their relative concentrations (which change with time in principle as the biological half-life is a function of mass for a set of similar compounds). This complex situation is tolerated because PEG is very useful.

Solid phase peptide synthesis yields well-defined polyamides of the repeating unit "—NH—Y—CO—" but requires protected derivatives and deprotection steps. Polyamides of the repeating unit —NH—Y—NH—CO—X—CO—, such as "—NH—$(CH_2)_6$—NH—CO—$(CH_2)_4$—CO—" (e.g. Nylon 66) are made by polymerizing diacids with diamines. This synthesis, along with more recent techniques involving solution polymerization of diacids with diamines, yields a product having a wide range of chain lengths. The absence of protecting groups is largely responsible for the resulting heterogeneity of chain length in these polyamides.

In light of the many potential applications of materials modified with organic chain-like molecules, there is a need in the art for improved chains for use in modifying target macromolecules or materials, such as surfaces. Accordingly, there is a need for a method of producing such polymers, but having a determinable length, by automated solid phase synthesis without the need for protecting groups. In particular, there is a need for PEG-based chains of precise length (i.e., chains containing a —(CH$_2$CH$_2$O)$_m$— group, where m has a single value), as well as methods for constructing such chains. In this manner, the disadvantages inherent in and observed for the currently used PEG chains, both for medical and non-medical uses, can be overcome. The polyamide chains of precise length and methods provided in the present invention meet these needs and others as well.

SUMMARY OF THE INVENTION

The present invention relates to a new class of polymers, polyamide-based chains containing a precise number of repeating monomer units (—NH—Y—NH—CO—X—CO—), which are synthesized by automated solid phase synthesis without the need for protecting groups and where X and Y can be varied independently at each step. Dimers, branched constructions and multimeric molecules which display phage-derived binding peptides, are easily assembled with these precision length polyamide chains, which can usefully replace polypeptides and polyethyleneglycol as molecular spacers.

More particularly, the present invention provides a water soluble organic polyamide-based chain of precise length having a precise number of repeating units, based upon the building up by amide bond formation of a precise number of monomer units, along with a process for preparing such chains. This chain has the Formula (III):

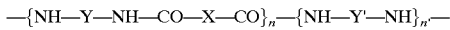

wherein: n is an integer from 1–100; n' is 0 or 1; X and Y are divalent organic radicals lacking reactive functional groups or are absent and are the same or different, and can vary independently with each of said repeating units; and Y' is a divalent organic radical lacking reactive functional groups or is absent.

More specifically, the present invention provides a polyethylene glycol-based chain of precise length, based upon a precise number of repeating polyethylene glycol-based units, along with a process for preparing such chains.

In essence, rather than increasing m in chains containing a —(CH$_2$CH$_2$O)$_m$— group (which leads to heterogeneity as m becomes large and takes a range of values rather than a discrete value), the present invention connects through amide bonds a series of monomer units containing a —(CH$_2$CH$_2$O)$_p$— group where p is small enough for the monomer unit to have a unique value of p rather than a range.

Another aspect of the subject invention is to provide methods and compounds for modifying under mild conditions a macromolecule (such as a protein, peptide, nucleic acid, liposome) or material such as a surface, with one or more polyamide chains of precise length.

In another aspect of the invention, the chain of Formula (III) where n' is 1 is synthesized by the steps of: (a) acylating the amino or hydroxyl group of a compound of the formula Z—Q-support, where Z is H$_2$N— or HO—; Q is a linker (which may be an amino acid residue) or a target molecule; and the support is a solid phase, matrix or surface, with a molar excess of a reagent L—CO—L', where L and L' are leaving groups and are the same or different; (b) aminolysing the product of step (a) with a molar excess of a diamine having the formula, NH$_2$—Y'—NH$_2$; (c) acylating the product of step (b) with a molar excess of a derivative of a diacid having the formula, HOOC—X—COOH; (d) activating the free carboxyl group of the product of step (c); (e) aminolysing the product of step (d) with a molar excess of a diamine having the formula, NH$_2$—Y—NH$_2$; and (f) optionally repeating steps (c)–(e) using a derivative of a diacid having formula HOOC—X—COOH and a diamine having formula NH$_2$—Y—NH$_2$, where said X and Y substituents are the same or different from the X and Y substituents used in any of the previous aminolysing and acylating steps.

In another aspect of the invention, the chain of Formula (III) where n' is 0 is synthesized by the steps of: (a) acylating the amino or hydroxyl group of a compound of the formula Z—Q-support with a molar excess of a derivative of a diacid having the formula, HOOC—X—COOH, where Z is H$_2$N— or HO—; Q is a linker or a target molecule; the support is a solid phase, matrix or surface; (b) activating the free carboxyl group of the product of step (a); (c) aminolysing the product of step (b) with a molar excess of a diamine having the formula, NH$_2$—Y—NH$_2$; and (d) optionally repeating steps (a)–(c) using HOOC—X—COOH and NH$_2$—Y—NH$_2$, where said X and Y substituents are the same or different from the X and Y substituents used in any of said previous acylating and aminolysing steps.

Another aspect of the invention is a water soluble organic polyamide-based composition having a precise number of repeating units, said composition having Formula (IV):

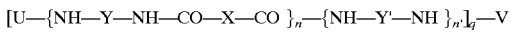

wherein: n is an integer from 1–100; n' is 0 or 1; q is an integer from 1 to 10; X and Y are divalent organic radicals lacking reactive functional groups or are absent and are the same or different, and can vary independently with each of said repeating units; Y' is a divalent organic radical lacking reactive functional groups or is absent; V is selected from the group consisting of: a monovalent or multivalent target molecule whose properties are being modified or enhanced and having an optional divalent spacer or linker; a reporter group having a multivalent linker; a reactive group; and a terminal group having a multivalent linker, said terminal group being selected from the group consisting of —OH, —NH$_2$, —H, and —Z—Q-support, where Z is a divalent spacer such as —NH—, —O— or may be absent, Q is a linker or a target molecule, and the support is a solid phase, matrix or surface; and U is selected from the group consisting of: a target molecule whose properties are being modified or enhanced, and having an optional divalent spacer or linker; a terminal group; a peptide chain; a protecting group; a support; and a reactive group.

Yet another aspect of the invention is a water soluble organic polyamide-based homogeneous composition having a precise number of repeating units, and having Formula (IV):

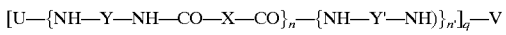

where: n is an integer from 1–100; n' is 0 or 1; q is an integer from 1 to 10; X and Y are divalent organic radicals lacking reactive functional groups or are absent and are the same or different, and can vary independently with each of said repeating units; Y' is a divalent organic radical lacking reactive functional groups or is absent; V is selected from the group consisting of: a target molecule which is a peptide of less than 50 amino acid residues and having an optional divalent spacer or linker; a reporter group having a multivalent linker; a reactive group; and a terminal group having a multivalent linker, said terminal group being selected from the group consisting of —OH, —NH$_2$, —H, and —Z—Q—support, where Z is a divalent spacer such as —NH—, —O— or may be absent, Q is a linker or a target molecule, and the support is a solid phase, matrix or surface; and U is selected from the group consisting of: a target molecule which is a peptide of less than 50 amino acid residues and having an optional divalent spacer or linker; a terminal group; a peptide chain; a protecting group; a support; and a reactive group; wherein at least one of U or V is a target molecule.

Yet another aspect of the invention provides for kits containing reagents suitable for synthesizing the water soluble organic polyamide-based chains, and kits containing either such reagents or such chains and a target molecule whose properties are to be modified or enhanced, having an optional divalent spacer or linker.

DESCRIPTION OF SPECIFIC EMBODIMENTS

In biochemistry and medicine, biocompatible molecular chains are needed to display binding modules on their tips (See for example, Kramer, et al., supra; Peters, et al., *Science* 282:1439 (1998); Johnson, et al., *Chemistry & Biology*, supra; and Terskikh, et al., *Proc. Natl. Acad. Sci. USA* 94:1663–1668 (1997)) as well as for other purposes (Zalipsky, *Bioconjugate Chemistry*, supra). Ideally, these chains should be of defined structure, i.e., length, rather than a mixture of chains of different lengths. Polypeptide chains offer one possibility but are in principle susceptible to proteolytic cleavage and might prove to be immunogenic. Polyethyleneglycol ("PEG") offers another possibility.

The present invention provides a method of producing a new class of biocompatible polymers which combine the advantages of both polypeptides (precise length, convenient synthesis) and PEG (flexible, amphiphilic, non-immunogenic, unsusceptible to proteases) and so can be used in lieu of conventional polypeptide or PEG molecular spacers for synthetic and semi-synthetic constructions.

By the methods of this invention, one is no longer limited to the few standard lengths of the commercial PEG linkers, and so length can be fine-tuned quite closely. This method also conveniently uses commercially available materials, is readily automated, and avoids protection and deprotection steps. Further, as expected for PEG-based molecules, the polyamides produced by the methods of the invention are completely soluble in water and in organic solvents such as dimethylformamide, but not in diethyl ether.

The present invention further provides a water soluble organic polymer-based chain of precise length, based upon the building up by amide bond formation of a precise number of repeating monomer units, along with a process for preparing such chains. Numerous organic precursors can be used in the chains of the invention. For purposes of illustration, and not limitation, the invention can be described by referencing monomers containing —CH$_2$CH$_2$O— units, and the resulting products is referred to as a polyethylene glycol-based ("PEG-based") chain. It is understood however, that reference herein to "PEG-based" chains is intended to mean any "water soluble polymer-based" or "water soluble organic" chain. Further, since the linker or chain is built up by amide bond formation, it is understood that the water soluble polymer-based chains of the invention are also properly referred to as "water soluble organic polyamide-based" chains. The terms "linker" and "chain" are used interchangeably as the chains of this invention find utility in linking targets together and in being attached to a single target.

Accordingly, the present invention provides a water soluble organic polyamide-based chain of precise length, based upon a precise number of monomer units. Very short chemical chains of precise length are used to build up, preferably on a solid phase, these water soluble organic polyamide-based chains of precise length. In particular, the invention uses very short chains of precise length to build up precise length PEG-based chains. Such short chains can be readily synthesized by those of skill in the art. In addition, some of these very short chains are commercially available and have been used in solution syntheses of short PEG linkers, as described in Wilbur, et al., *Bioconjugate Chemistry* 8:572–584 (1997).

The present invention also relates to methods for chemically modifying target molecules and surfaces (e.g. gold or glass), by means of covalent attachment of the polyamide-based chains of precise length described herein. These chains find particular utility in enhancing the properties of target molecules, for attaching additional molecules (such as a fluorophore, metal chelator or other reporter group, or a drug molecule) to a target molecule, and to attach several smaller target molecules together to form a larger one with enhanced properties (dimer, trimer, tetramer and higher oligomer). This invention also contemplates use of the water soluble organic polyamide-based chains to modify surfaces such as such as gold or glass or plastics for biosensor and other applications.

The term "target molecule" refers to a monovalent or multivalent target molecule, particularly a macromolecule, whose properties are being modified or enhanced by attachment to the water soluble organic polyamide-based chains of precise length described herein. Such target molecules can be organic molecules (which include molecules of biologic origin as well as organic molecules with inorganic components) having a molecular weight of at least 100 and up to or greater than 10,000. Typically such organic molecules will have a molecular weight of at least 1000, more typically in the range of about 1000–2000. Typically, the target molecule will be a biologically important protein, polypeptides, peptides, amino acids, nucleic acid, liposome, or therapeutic agent. Exemplary target molecules, include by way of illustration and not limitation, plasma proteins such as fibrinogen, immunoglobulins or fragments thereof, hormones such as insulin, cytokines such as tumor necrosis factor and enzymes such as tissue plasminogen activator. The target molecule can be derived from natural or recombinant sources, or can be synthetic such as a fluorophore, metal chelator or other reporter group. When the target molecule is multivalent, it may be attached to several chains of the invention. To allow for further enhancement or modification of a target molecule, the target molecule may have a multivalent linker between it and the chain.

In another embodiment of the invention, reduction of the polyamide chains with LiAlH$_4$, or diborane provides a new class of polyamines which may have the useful properties of ethyleneimine (see, for example, Ferrari, et al., *Gene Ther.* 4:1100–1106 (1997)) while also permitting total control over structure (linearity, length, hydrophobicity, charge spacing).

In general, the method of the invention is a three-step solid phase procedure involving commercially available diamines (or derivatives), shown here as a short diamine monomer of Formula (I):

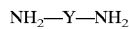

and commercially available diacids, shown here as a short diacid monomer of Formula (II):

HOOC—X—COOH in a form activated to permit acylation (such as the cyclic anhydride), referred to herein as "a derivative of a diacid".

The X and Y substituents are independently selected from the group consisting of divalent organic radicals that lack reactive functional groups, or are absent. X and Y can be the same or different. Suitable divalent organic radicals are non-reacting groups such as substituted or unsubstituted, branched or linear, aliphatic or aromatic groups such as phenyl or $C_1$–$C_{10}$ alkylene moieties, $C_1$–$C_{10}$ alkyl groups, or a combination thereof, and may optionally contain one or more heteroatoms. Exemplary divalent organic radicals include, by way of illustration and not limitation, alkyl groups such as —$(CH_2)_2$— and —$(CH_2)_6$—; and alkyl groups containing heteroatoms such as —$(CH_2)_3$—$(OCH_2CH_2)_3$—$CH_2$—, —$[(CH_2)_3$—O—$(CH_2)_2$—$(CH_2)_2$—O—$(CH_2)_3]$—, —$CH_2$—O—$CH_2$—, and —$CH_2$—N$(CH_3)$—$CH_2$—, and so forth.

As used herein the term "reactive functional group" means by way of illustration and not limitation, any free amino, carboxyl, thiol, alkyl halide, hydroxy or aldehyde group. It is important that the short monomer starting materials not have any functionalities that will interfere with the acylation, activation and aminolysis steps of the invention, as will be described in detail later. However, such reactive functional groups may be present on X or Y if they are protected rendering them non-reactive, for example, a protected amino group may be present. For example, the X and Y substituents may contain an amino group protected by tert-butyloxycarbonyl (Boc). Note, however, that 9-Fluorenylmethyloxycarbonyl (Fmoc) is not well suitable as a protecting group for an amino group within X or Y since it cannot withstand the aminolysis conditions.

It is preferred that the monomers of Formula (I) and (II), and therefore the X and Y substituents, be symmetrical, otherwise the end groups (amino or carboxyl) would be distinguishable and heterogeneity would result. For example, succinic acid (as its anhydride, where the X substituent is the radical, —$CH_2CH_2$—) is symmetrical and only gives one amide product in an acylation, HOOCCH$_2$CH$_2$CO—NH—, and therefore is a suitable diacid. Methylsuccinic anhydride can give two products, HOOCCH(Me)CH$_2$CO—NH— and HOOCCH$_2$CH(Me)CO—NH—, and therefore is less suitable.

Preferably, the short monomer of either Formula (I) or (II) is a water soluble polymer-based monomer such that either X, Y, or both substituents is a divalent organic radical of precise length containing about 1 to 5 polymer groups. In a preferred embodiment, either X or Y or both are divalent organic radicals containing about 1 to 5 PEG (—$CH_2CH_2O$—) groups. Symmetry is preserved by judicious choice of the terminal end groups, for example, as in —$CH_2CH_2CH_2(OCH_2CH_2)_pCH_2$—, where p is an integer from 1 to 5 but takes a discrete value for a given compound of Formula (I) or (II). Numerous other groups are suitable for use in the invention in place of the PEG groups. These include, by way of illustration and not limitation, methylene, propylene glycol and its oligomers (i.e., (—$CH_2CH_2CH_2O$—)$_p$), defined copolymers of —$CH_2CH_2O$— and —$CH_2CH_2CH_2O$— groups, defined oligomers of tetrahydrofuran, and defined oligomers of vinylpyrrolidone.

One of the most useful short PEG-based symmetrical diamines of precise length is 4,7,10-trioxa-1,13-tridecanediamine (Fluka Chemicals, Buchs, Switzerland):

NH$_2$—(CH$_2$)$_3$—(OCH$_2$CH$_2$)$_3$—CH$_2$—NH$_2$ 4,7,10-trioxa-1,13-tridecanediamine is a diamine monomer of Formula (I) where Y contains three polyethylene glycol groups (—OCH$_2$CH$_2$—) and has the symmetrical formula:

—(CH$_2$CH$_2$CH$_2$—O—CH$_2$CH$_2$)—O—(CH$_2$CH$_2$—O—CH$_2$CH$_2$—CH$_2$)—

A desirable characteristic of this material is that it is supplied with three PEG groups, as shown above, and is essentially exempt of homologous compounds having one, two, four or even five PEG groups. This exemplifies what is intended when a monomer unit is said to be of "precise length". A polyamide made with such material will also be of precise length provided it is made in a discrete number of steps and not by uncontrolled polymerization with a diacid as is conventionally performed. It will be referred to as a PEG-based chain or linker, even though the PEG units (—OCH$_2$CH$_2$—) are interrupted at intervals by amide bonds or other groups.

Monomer units similar to 4,7,10-trioxa-1,13-tridecanediamine, but having either one, two, four or even five PEG groups, can also be readily synthesized by methods that are well known in the art. Such monomers would be essentially exempt of homologous compounds having a different number of PEG groups.

A non-PEG-based diamine of precise length that is also useful in the present invention is a 4,9-dioxa-1,12-dodecanediamine of the formula:

NH$_2$—(CH$_2$)$_3$—O(CH$_2$)$_4$—O—(CH$_2$)$_3$—NH$_2$ which is described in Johnson, et al., *Bioconjugate Chemistry* 8:447–452 (1997). Here, Y has the symmetrical formula:

—[(CH$_2$)$_3$—O—(CH$_2$)$_2$]—[(CH$_2$)$_2$—O—(CH$_2$)$_3$]—

This same article illustrates examples of activated forms of the diacid component, such as the anhydrides of HOOC—CH$_2$OCH$_2$—COOH and HOOC—CH$_2$N(CH$_3$)CH$_2$—COOH.

Another non-PEG based diamine that is useful in the method of the inventions is 1,6-diaminohexane, NH$_2$—(CH$_2$)$_6$—NH$_2$ ("DAH"). In addition, there are numerous commercially available diacids and diamines, an extensive list of which is described in Hai, et al., supra, which is incorporated herein by reference. As will be described below, it is possible, by selecting an appropriate diacid and diamine for each step, to modulate factors such as hydrophobicity along the length of the chain (described herein using diamines such as 1,6-diaminohexane), to add reactive groups to the chain termini such as oxime-forming groups, and to extend the chain by standard techniques of peptide synthesis.

Preferred diacids of Formula (II) include, by way of illustration, and not limitation, HOOC—CH$_2$CH$_2$—COOH.

In general, the method of the invention is a three-step solid phase procedure involving a diamine of Formula (I) and derivative of a diacid, said diacid having Formula (II), shown here for the case of an amino-containing resin (NH$_2$-Resin). This procedure does not require the use of protecting groups. Step I is an acylation step using a derivative of a diacid:

HOOC—X—COOH+NH$_2$-Resin→HOOC—X—CONH-Resin

Step 2 is an activation step using, for example, carbonyldiimidazole:

HOOC—X—CONH-Resin+carbonyldiimidazole→imidazolyl-

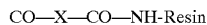

Finally, Step 3 is an aminolysis step using a diamine:

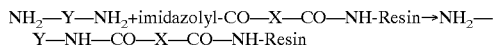

In the preferred methods of the invention, at least one of X and Y is present, and more preferably both are present. However, the invention does contemplate use of compounds of Formulas (I) and (II) where X, Y or both may be absent. A special case is that of the diacid carbonic acid, where —CO— replaces —CO—X—CO—, the repeat unit becomes —NH—Y—NH—CO— and the product is then more correctly termed a polyurea, which is a type of polyamide. In this special case, the acylation step and the activation step are combined in a single step, using carbonyldiimidazole, which is a convenient form of di-activated carbonic acid:

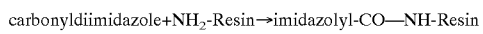

The imidazolyl-CO—NH-Resin is then directly ready for aminolysis using a diamine:

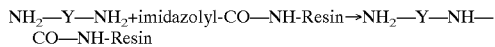

As indicated above, monomer units of Formula (I) and (II) are used to build up chains of precise length, i.e., having a precise number of the repeating monomer unit, —NH—Y—NH—CO—X—CO—. In one aspect of the invention, each cycle of the synthesis uses the same diamine of Formula (I), $NH_2$—Y—$NH_2$, and the same diacid of Formula (II), HOOC—X—COOH. Accordingly, in one aspect of the invention, monomer units of Formulas (I) and (II) are used to build up water soluble organic polyamide-based chains having a precise number of repeating units, said chains having Formula (III): —(NH—Y—NH—CO—X—CO)$_n$—(NH—Y'—NH)$_{n'}$—, where: n is an integer from 1–100; n' is 0 or 1; X and Y are divalent organic radicals lacking reactive functional groups or are absent and are the same or different, and can vary independently with each of said repeating units; and Y' is a divalent organic radical lacking reactive functional groups or is absent.

It is important to note that the X substituent, the Y substituent, or both substituents can be varied independently at each step of the synthesis if desired, and need not be identical throughout. There are several reasons for varying X and/or Y during the synthesis of the linker, with one of the most valuable being the ability to modulate hydrophobicity along the length of the linker, including making parts such as one end of the linker more hydrophilic or hydrophobic than other parts. This is readily accomplished by using one or more different diamines of Formula (I), $NH_2$—Y—$NH_2$, and/or one or more different diacids of Formula (II), HOOC—X—COOH, in subsequent cycles of the chain synthesis, i.e., the X and Y substituents may be chosen independently at each acylation and aminolysis step.

In another preferred embodiment, at least one of X and Y substituents contains from about 1 to 5—$CH_2CH_2O$— groups. This is achieved by having either Formula (I) or (II), or both, as PEG-based monomers. In this manner X can have the formula —a—$(CH_2CH_2O)_p$—b— and/or Y can have the formula —a'—$(CH_2CH_2O)_{p'}$—b'—, where a, a', b and b' would be divalent organic radicals lacking reactive functional groups, or would be absent, and can be the same or different. The a, a', b and b' substituents are preferably chosen so as to preserve symmetry of the monomer unit as described above. The integers p and p' are from about 1 to 5, but can be zero. A preferred polyamide-based linker of the invention would then have one of the following variations of Formula (III):

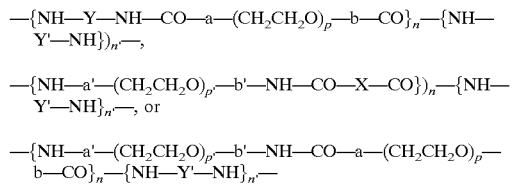

where a, a', b, b', p and p' are as defined above. Alternately, if the polyamide-based linker is to be used for a non-pharmaceutical purpose, p and p' can be 0. It is important to note that a, a', b, b', p, and p' can be varied independently for both the diacid component and the diamine component at each step of the synthesis of the linker, should this be desired, as is described above for Formula (III). In this manner X, the —a—$(CH_2CH_2O)_p$—b— formula, and Y, the —a'—$(CH_2CH_2O)_{p'}$—b'— formula, can appear in numerous combinations along the length of the linker of the invention. One reason for introducing such variation is to cause variation in hydrophobicity and hydrophilicity along the length of the linker; another might be to introduce a charged group for example with X being —$CH_2N(CH_3)CH_2$—.

The following precise length chains are illustrative of the invention, and are not intended to be limiting in any manner. A particularly preferred chain of the invention is a PEG-based chain of Formula (III), where Y is —a'—$(CH_2CH_2O)_{p'}$—b'—, where a' is —$CH_2$—, b' is —$(CH_2)_3$—, and p' is 3, n' is 0 and X is —$(CH_2)_2$—:

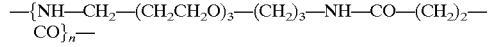

which can also be written as:

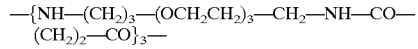

This chain can also be referred to as a —('PEG'-succ)$_n$— chain, where 'PEG' represents the formula —NH—$(CH_2)_3$—$(OCH_2CH_2)_3$—$CH_2$—NH—, and succ represents the formula —CO—$(CH_2)_2$—CO—. Examples of such chains include —('PEG'-succ)$_3$— and —('PEG'-succ)$_8$—. The —('PEG'-succ)$_n$— chain is also exemplary of those chains of the invention where the X and Y substituents remain the same in each repeating monomer unit. Other such chains include, by way of example, —('PEG'-succ)$_n$—'PEG'—, such as —('PEG'-succ)$_{16}$—'PEG'—; and —('DAH'-succ)$_n$—, where 'DAH' represents the formula —NH—$(CH_2)_6$—NH—.

Exemplary of those chains of the invention where the X and Y substituents vary in the repeating monomer units include, by way of example, —('DAH'-succ-'PEG'-succ)$_n$— and —('DAH'-succ-'PEG'-succ)$_z$—'DAH'-succ-'PEG'—, where z is an integer from 1–49. Although there are two Y substituents used in these examples it is understood that more than two different Y substituents may be used in the chains of the invention. In addition, in these examples X remains the same; however, it is understood that X may vary just as is illustrated for the Y substituent.

The polyamide chains of Formula (III) can easily be incorporated, as a central repeating unit —(NH—Y—NH—CO—X—CO)—, into a water soluble organic polyamide-based composition or material, i.e., a "product".

Accordingly, in one embodiment of the invention, a single V or U substituent (as defined below) may be modified or enhanced by the attachment of one or more chains of the invention. Such a water soluble organic polyamide-based composition having a precise number of repeating units, has Formula (IV):

[U—{NH—Y—NH—CO—X—CO}$_n$—{NH—Y'—NH)}$_{n'}$]$_q$—V where: n is an integer from 1–100; n' is 0 or 1; q is an integer from 1 to 10; X and Y are divalent organic radicals lacking reactive functional groups or are absent and are the same or different, and can vary independently with each of said repeating units; Y' is a divalent organic radical lacking reactive functional groups or is absent; V is selected from the group consisting of: a monovalent or multivalent target molecule whose properties are being modified or enhanced and having an optional divalent spacer or linker; a reporter group having a multivalent linker; a reactive group; and a terminal group having a multivalent linker, said terminal group being selected from the group consisting of —OH, —NH$_2$, —H, and —Z—Q-support, where Z is a divalent spacer such as —NH—, —O— or may be absent, Q is a linker or a target molecule, and the support is a solid phase, matrix or surface; and U is selected from the group consisting of: a target molecule whose properties are being modified or enhanced, and having an optional divalent spacer or linker; a terminal group; a peptide chain; a protecting group; a support; and a reactive group. As noted above, the X and Y substituents can be varied during synthesis of the chain.

In its simplest form, the composition of Formula (IV), where q is 1, comprises a U and V group, linked by a chain of the invention: U—{NH—Y—NH—CO—X—CO}$_n$—{NH—Y'—NH}$_{n'}$—V It is understood that the present invention describes chains and methods for their synthesis, whereas the groups U and V are described by way of example only and are not intended to be limiting in any manner. V can be a monovalent or multivalent target molecule whose properties are being modified or enhanced and having an optional divalent spacer or linker, such as an oxime linker. V can also be a reporter group such as a fluorophore or metal chelator having a multivalent linker. As used herein the term "multivalent" is intended to means having a valency greater than one, and includes the term "divalent".

V can be further be a reactive group such as is well known in the art, for example, reactive groups suited for the cross-linking of polymers or the conjugation of biomolecules. Examples include, by way of illustration and not limitation, bromoacetyl, aminoacyl such as Tyr- or Ser-, aminooxyacetyl, glyoxylyl, mercaptoacetyl, mercaptopropionyl. In addition, numerous groups useful for the conjugation of biomolecules are discussed in *Bioconjugate Techniques*, Hermanson, G. T., Academic Press, San Diego, 1996.

V can also be a terminal group having a multivalent linker, said terminal group being selected from the group consisting of —OH, —NH$_2$, —H, and —Z—Q-support, where Z is a divalent spacer such as —NH—, —O— or may be absent, Q is a linker or a target molecule, and the support is a solid phase, matrix or surface, such as by way of illustration and not limitation, natural and synthetic resins; cells and membranes; silicon chips; sensor chips; gold, glass, plastic and other biosensor surfaces; and tissue culture plates.

Examples of suitable bivalent and divalent organic radicals as the "Q" substituent or the spacer/linker attached to the target molecule, include, by way of illustration and not limitation, the Sasrin linker —CH$_2$(C$_6$H$_3$(OCH$_3$))—O—CH$_2$—, —C(O)O—CH$_2$(C$_6$H$_3$(OCH$_3$))—O—CH$_2$—, an aminooxyacetyl (NH$_2$OCH$_2$CO—) linker, —COCH$_2$ON=CH—CO—, —CH=NOCH$_2$CO— and so forth.

As noted above, the Q substituent can be a target molecule. Typically, this will occur when the target molecule is a peptide that has been synthesized using the well known solid phase techniques, and forms a part of the Z—Q-support reagent used in the synthesis of the linker. The terminal group may contain a reactive group (such as an alkyl thiol) through which to couple a target molecule. This reactive group is protected (or attached through orthogonal protection/deprotection strategies after the building up of the PEG-based linker). Orthogonal protection strategies are well known in the art. See *Methods in Enzymology* Vol. 289. In a preferred embodiment, V is a monovalent or multivalent target molecule, for example, a macromolecule, or a solid phase or matrix, whose properties are being modified or enhanced by the linker of the invention.

U is selected from the group consisting of: a target molecule whose properties are being modified or enhanced, and having an optional divalent spacer or linker, such as an oxime linker; a terminal group selected from the group consisting of H—, HC(O)CO—, NH$_2$OCH$_2$CO—, and an aliphatic acyl group; a peptide chain, which includes a single peptide chain or a polypeptide chain; a protecting group such as Boc or Fmoc; a support such as a solid phase or matrix; and a reactive group as described above.

In a preferred embodiment, at least one of U or V is a target molecule whose properties are being modified or enhanced by linkage to the polyamide-based linkers of precise length. Such "target molecules", as defined above, are organic molecules that are preferably biologically important proteins, polypeptides, peptides, nucleic acids, liposomes, or therapeutic agents. In another preferred embodiment, at least one of U or V is a target molecule which is a peptide of less than 50 amino acid residues and having an optional divalent spacer or linker.

The following compositions are illustrative of the invention, and are not intended to be limiting in any manner. Exemplary compositions of Formula (IV) include:

H—('PEG'-succ)$_n$—'PEG'—H, where U and V are hydrogen terminal groups and n is, for example, 7;

H—Ser—('PEG'-succ)$_n$—'PEG'—Ser—H, where U and V are amino acids and n is, for example, 16;

(peptide)-oxime-('PEG'-succ)$_n$—'PEG'-oxime-(peptide), where U and V are peptides having an oxime linker, for example erythropoietin mimetic peptides ("EMP") having —COCH$_2$ON=CH—CO— linkers, such as
amide-GRLPQCVWTMPGMHCAYLGG-
—COCH$_2$ON=CHC(O)—('PEG'-succ)$_n$—'PEG'—C(O)CH=NOCH$_2$CO—
—GGLYACHMGPMTWVCQPLRG-amide containing two copies of the amino acid residues of (SEQ ID NO:1),
  and n is, for example, 12 or 16;

H—('PEG'-succ)$_n$-Leu-PAM resin, where U is H, and V is —Z—Q-support, where Z is absent, Q is an amino acid residue (Leu) and the support is PAM resin;

H—Tyr—('PEG'-succ)$_n$-Leu—OH, where U is an aminoacyl group (Tyr-), V is an amino acid residue (Leu) n is, for example, 3;

peptide-Lys(NH$_2$OCH$_2$CO—('PEG'-succ)$_n$)—NH$_2$, where U is an aminooxyacetyl group ($NH_2OCH_2CO$—), and V is a target peptide molecule, with a linker, -Lys amide, for example H-Ser-Val-Trp-Arg-Trp-Leu-Pro-Tyr-Asp-Lys-Tyr-Glu-Lys ($NH_2OCH_2CO$—('PEG'-succ)$_8$)—$NH_2$ (SEQ ID NO:4 or SEQ ID NO:3 plus lysine as part of the linker), n is, for example, 8;

H-Ser-('PEG'-succ)$_n$-Abu—OH, where U is an aminoacyl group (Ser-), V is the target molecule aminobutyric acid n is, for example, 8;

H—('DAH'-succ-'PEG'-succ)$_n$—'DAH'-succ-'PEG'—H, where U and V are both hydrogen terminal groups n is, for example, 3;

Peptide-('PEG'-succ)$_n$-Lys(AoA)-amide (SEQ ID NO:6), where AoA is aminooxyacetyl and n is, for example, 8. The target peptide molecule can be, for example, -ADGACRNPWC- (SEQ ID NO:6); and As shown above, the chains of the invention may be used to modify numerous target peptides, in particular peptides of less than 50 amino acid residues and having appropriate terminal groups such as, by way of illustration and not limitation, -GGLYACHMGPMTWVCQPLRG- (SEQ ID NO:1); -SVWRWLPYDKYE- (SEQ ID NO:3); and -ADGACRNPWC- (SEQ ID NO:6), to provide homogeneous compositions.

The compositions of the invention may also utilize several chains to form a branched structure. For example, one exemplary composition is a branched composition of Formula (IV), where U is a an aminoacyl group (Ser-) and V is a multivalent target molecule Lys$_2$Lys-NHCH$_2$CH$_2$SH. A lysine "tree" was first synthesized having four free amino groups. Four cycles created four linkers of formula H-Ser-('PEG'-succ)$_4$—, each linker being attached to one of the four free amino groups: (H-Ser-('PEG'-succ)$_4$)$_4$Lys$_2$Lys-NHCH$_2$CH$_2$SH.

Another example of a branched composition is a homogeneous branched composition of Formula (IV), where U is a peptide having an oxime linker and V is an amino acid (Lys): (peptide)-oxime-('PEG'-succ)$_n$-Lys((peptide)-oxime-('PEG'-succ)$_n$)amide, where an exemplary peptide is -GGLYACHMGPMTWVCQPLRG- (SEQ ID NO:1) and n is, for example, 2.

Yet another example of a branched composition is a homogeneous branched composition of the formula [peptide-('PEG'-succ)$_n$-Lys(oxime)amide]$_9$Lys$_2$Lys-NHCH$_2$CH$_2$S—CH$_2$C(O)NH— reporter group, where U is a target peptide and V is a reporter group having a multivalent linker -Lys(AoA)amide-Lys$_2$Lys-NHCH$_2$CH$_2$S—CH$_2$C(O)NH—, for example [peptide-('PEG'-succ)$_8$-Lys(oxime)amide]$_4$Lys$_2$Lys-NHCH$_2$CH$_2$S—CH$_2$C(O)NH—fluorescein, where there are four copies of the target peptide molecule, for example, -ADGACRNPWC- (SEQ ID NO:6).

The polyamide precise length chains of Formula (III), where n' is 0, are readily synthesized by a three step synthesis shown in Scheme I-A, which involves an acylation step, an activation step and an aminolysis step. Standard techniques of solid phase synthesis (Fields, ed., Solid phase peptide synthesis, *Meth. Enzymol.* 289) can be used both with a suitably programmed ABI 430A instrument or a home-built machine. The reactions may also be performed quite easily manually, although this is more time consuming and less convenient. In the special case of the diacid carbonic acid, the acylation and activation steps occurs together as explained above.

In one embodiment of the invention, a water soluble organic polyamide-based chain having a precise number of repeating units and having Formula (III), where n' is 1:

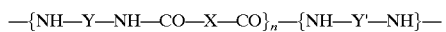

where: n is an integer from 1–100; X and Y are divalent organic radicals lacking reactive functional groups or are absent and are the same or different, and can vary independently with each of said repeating units; and Y' is a divalent organic radical lacking reactive functional groups or is absent; is synthesized by a method comprising the steps of: (a) acylating the amino or hydroxyl group of a compound of the formula Z—Q-support, where Z is H$_2$N— or HO—; Q is a linker or a target molecule; and the support is a solid phase, matrix or surface, with a molar excess of a reagent L—CO—L', where L and L' are leaving groups and are the same or different; (b) aminolysing the product of step (a) with a molar excess of a diamine having the formula, NH$_2$—Y'—NH$_2$; (c) acylating the product of step (b) with a molar excess of a derivative of a diacid having the formula, HOOC—X—COOH; (d) activating the free carboxyl group of the product of step (c); (e) aminolysing the product of step (d) with a molar excess of a diamine having the formula, NH$_2$—Y—NH$_2$; and (f) optionally repeating steps (c)–(e) using a derivative of a diacid having formula HOOC—X—COOH and a diamine having formula NH$_2$—Y—NH$_2$, where said X and Y substituents are the same or different from the X and Y substituents used in any of said previous aminolysing and acylating steps.

This method encompasses leaving the linker bound to the support, for example for packaging with a suitable carrier in a kit, for subsequent attachment to a target molecule. However, the method also encompasses Q being a linker containing a cleavable moiety or a target molecule bound to the support by a linker containing a cleavable moiety, and the method further comprises the step of cleaving the cleavable moiety to release the water soluble organic polyamide-based chain of precise length from the support.

As used herein, the term "cleavable moiety" is intended to mean a moiety that is capable of being selectively cleaved to release the polyamide-based linker or target molecule from the solid phase. The cleavable moiety must be capable of resisting cleavage under conditions suitable for the acylation, activation and aminolysis steps of the invention. Such cleavable moieties are well known to those of skill in the art.

The optional repeating steps can utilize diacids and diamine where the X and Y substituents do not vary, thus producing a chain of identical repeat units such as:

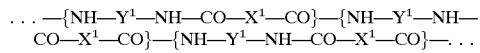

However, using at least one diacid or at least one diamine having a different Y or X substituent than used in the previous aminolysis or acylating step, respectively, will provide for a chain where the repeat units are varied, such as:

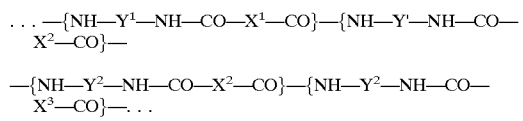

One preferred method of the invention is presented below as Scheme I-A.

SCHEME I-A

Acylation Step

A resin suitable for solid phase peptide synthesis is used, for example, Z—Q-support, where Z is NH$_2$— or HO— and Q is defined as Q above, but is typically a bivalent organic radical. An activated form of the diacid derivative of Formula (II), HOOC—X—COOH, is used to acylate the amino groups (or the hydroxyl group) attached to the support. The cyclic anhydride of the diacid succinic acid, HOOC—CH$_2$—CH$_2$—COOH, Formula (II) where X is —CH$_2$—CH$_2$—, is particularly well suited for use in the acylation step. In the case where a cyclic anhydride is used:

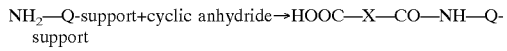

or

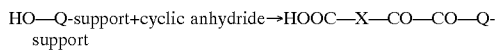

In a typical acylation step of the invention, the resin is first swollen in a suitable solvent, then acylated with an excess of the activated form of the diacid (which is dissolved in a suitable solvent) by vortex mixing at room temperature. A base such as N,N-diisopropylethylamine ("DIEA") or 4-dimethylaminopyridine ("DMAP"), and additives such as N-hydroxybenzotriazole ("HOBT") are usually added to assist the acylation, according to techniques known to those skilled in the art of peptide synthesis (*Methods in Enzymology* Vol. 289). When a hydroxy resin (e.g., Sasrin resin from Bachem, Switzerland) is being acylated, DMAP is preferably present and the acylation is repeated a second time to force the acylation to completion. When an amino resin is being acylated (NH$_2$-Q-support), it is recommended that the Kaiser test (Kaiser, et al., *Analyt. Biochem.* 84:595 (1970) or *Methods in Enzymology* Vol. 289, p. 54) be performed to verify that acylation is complete, before proceeding with the activation step. An excess of acylating reagent is used to drive the reaction to completion, otherwise chains lacking a number of repeat units will accumulate after several cycles as is the case for solid phase peptide synthesis.

For example, an amino resin such as Boc-Leu-Pam resin (0.5 g, approximately 0.3 mmole) is swollen in dimethylformamide ("DMF"), deprotected to yield H-Leu-Pam resin. The resin is then acylated with 4 mmole succinic anhydride ("SA") by vortex mixing at room temperature for 10 to 30 minutes. SA is dissolved in 8 ml DMF (Burdick and Jackson High Purity grade) which is 0.5 M in HOBT and to which 400 µl DIEA is added. After draining and washing the resin with DMF, the Kaiser ninhydrin test is performed to establish that acylation is complete. If not, the acylation step is repeated.

If a naked resin is used (e.g. Sasrin, Bachem), 0.5 M DMAP can be used in place of the HOBT, with coupling time along the order of 30 minutes (versus 10 minutes when an amino resin is used), and the coupling step is repeated once.

Activation Step

The activation step involves activation of the free carboxyl group, i.e., activation of the acid group not attached to the chain. This activation step is necessary when a cyclic anhydride is used in the acylation step since the carboxyl group not attached to the chain is a free carboxyl group (the case where a doubly activated diacid is used for the acylation step is discussed in Scheme II). Activation attaches a leaving group to the free carboxyl group:

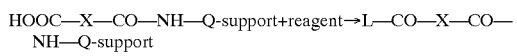

or

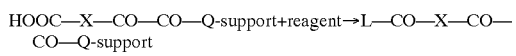

The reagents used in this activation step are those known to the art (*Methods in Enzymology* Vol. 289 and references therein) which attach a leaving group "L" to the free carboxyl group. It is preferable to employ an excess of activating agent to activate essentially all of the carboxyl groups and so avoid the accumulation of chains lacking a number of repeat units. Suitable reagents are those which may be used in excess without side reactions, and include carbonyl diimidazole ("CDI", which creates a mixed anhydride imidazolyl-CO—O—CO—X-etc. or an acyl imidazole imidazolyl-CO—X-etc.) and disuccinimidyl carbonate (which creates a hydroxy succinimidyl ester). Activating agents such as O-(7-azabenzotriazol-1-yl)-1,1,3,3-tetramethyluronium hexafluorophosphate ("HATU") may also be used successfully and are employed in only a slight excess over free carboxyl groups.

In a typical activation step of the invention, after draining and washing the resin with a suitable solvent, the free carboxyl group is activated with an activating reagent such as CDI, using caution to insure that the CDI is stored properly as it is sensitive to humidity. For example, after draining and washing the resin with DMF, the free carboxyl group is activated with 8 mmole of CDI (Fluka) in 8 ml DMF for 30 minutes with vortex mixing.

In actuality activation with CDI can be viewed as a two step process, where activation of the carboxylic acid with CDI first forms an imidazolyl anhydride (where "im" is an imidazole radical or imidazolyl):

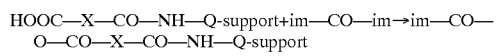

This anhydride may then react with displaced imidazole molecules to yield:

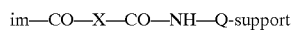

which undergoes aminolysis in the aminolysis step to give:

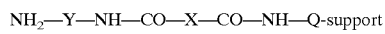

or the anhydride may undergo direct aminolysis to yield the same product:

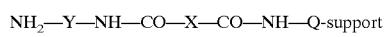

Either way, the desired product is formed. See Aslam, et al., *Bioconjugation*, page 387 (Macmillan Reference, 1998).

Aminolysis Step

The aminolysis step involves addition of a diamine of Formula (I), NH$_2$—Y—NH$_2$, of homogeneous length:

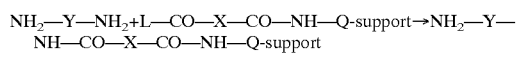

or

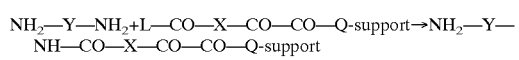

In a typical aminolysis step of the invention, after draining and washing with a suitable solvent, the resin-bound material is aminolysed with a large excess of a diamine of Formula (I). After thorough washing, the Kaiser ninhydrin test shows the characteristic blue color and the amino resin is ready for the next acylation/activation/aminolysis cycle.

The diamine, 4,7,10-trioxa-1,13-tridecanediamine, is particularly well suited for use in the aminolysis step.

For example, after a brief drain and wash with DMF, the resin-bound imidazolide is aminolysed with a PEG-based diamine (e.g. 4,7,10-trioxa-1,13-tridecanediamine, Fluka, 4 ml diamine premixed with 4 ml DMF which is 0.5 M in HOBT) for to 60 minutes with vortex mixing. After thorough washing with DMF, the Kaiser test shows the characteristic blue color and the amino resin is ready for the next acylation/activation/aminolysis cycle, i.e., after washing, the amino group is acylated again with SA to lengthen the chain, etc. It is important to note that some hydrophobic diamines, such as 1,6-diaminohexane, may require use of N-methylpyrrolidone in place of DMF in all three steps (acylation, activation and aminolysis).

The acylation, activation and aminolysis steps may thus be repeated once to add a second —NH—Y—NH—CO—X—CO— unit, yielding:

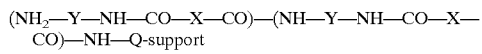

or

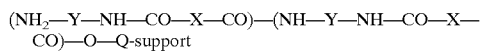

and so on. One cycle of the acylation, activation and aminolysis steps yields (NH$_2$—Y—NH—CO—X—CO)—Z—Q-support. Several repeating cycles of the acylation, activation and aminolysis steps, yields a chain of Formula (III), —(NH—Y—NH—CO—X—CO)$_n$— (where n' is 0) or a product of Formula (IV), [U{NH—Y—NH—CO—X—CO}$_n$]$_q$—V, where, for example, U is H and V is —Z—Q-support, n' is 0 and n is the number of repeating cycles. For example, when the cycle of acylation, activation and aminolysis is done twice using succinic anhydride and 4,7,10-trioxa-1,13-tridecanediamine, the synthesis provides for an exemplary PEG-based linker:

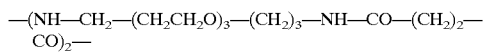

or the product:

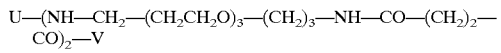

where U is H and V is —Z—Q-support.

In another embodiment of the invention, a water soluble organic polyamide-based chain having a precise number of repeating units and having Formula (III), where n' is 0:

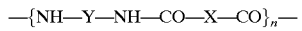

where: n is an integer from 1–100; X and Y are divalent organic radicals lacking reactive functional groups or are absent and are the same or different, and can vary independently with each of said repeating units; is synthesized by a method comprising the steps of: (a) acylating the amino or hydroxyl group of a compound of the formula Z—Q-support with a molar excess of a derivative of a diacid having the formula, HOOC—X—COOH, where Z is H$_2$N— or HO—; Q is a linker or a target molecule; the support is a solid phase, matrix or surface; (b) activating the free carboxyl group of the product of step (a); (c) aminolysing the product of step (b) with a molar excess of a diamine having the formula, NH$_2$—Y—NH$_2$; and (d) optionally repeating steps (a)–(c) using HOOC—X—COOH and NH$_2$—Y—NH$_2$, where said X and Y substituents are the same or different from the X and Y substituents used in any of said previous acylating and aminolysing steps.

As noted above, this method also encompasses leaving the linker bound to the support or cleaving it from the support by means of a cleavable moiety present as the linker Q or in the linker binding the target molecule Q to the support. Further, this method also contemplates using the same or different X and Y substituents during the steps of the synthesis.

Another preferred method of the invention is presented below as Scheme I-B, which is a modification of Scheme I-A, where the acylation step in the first cycle has omitted, but is included in subsequent cycles. In this manner, Scheme I-B involves an activation step and an aminolysis step, following by one or more cycles of the acylation/activation/aminolysis steps. The reactions and reagents used are the same as those described above in Scheme I-A.

SCHEME I-B

Activation Step

A resin suitable for solid phase peptide synthesis is used, preferably one having an appropriate acid-cleavable hydroxyl linker, for example, a Sasrin resin (HO—CH$_2$—(C$_6$H$_3$(OCH$_3$))—O—CH$_2$-resin) or one having an amino group. First, the resin is swollen in a suitable solvent. Then, in a typical activation first step of the invention, the hydroxyl (or amino) group of the resin of formula Z—Q-support is activated. Activation with a reagent such as CDI acylates the hydroxyl (or amino) groups with a group which still possesses a leaving group (HO— becomes im-CO—O— and NH$_2$— becomes im-CO—NH—): HO—CH$_2$(C$_6$H$_3$(OCH$_3$))—O—CH$_2$-support+reagent→L—COO—CH$_2$((C$_6$H$_3$(OCH$_3$))—O—CH$_2$-support where L is a leaving group.

After draining and washing the activation step may be repeated.

Aminolysis Step

The aminolysis step is as described above, where a diamine of Formula (I), NH$_2$—Y'—NH$_2$, of homogeneous length is added to the activated resin. For example, after a brief drain and wash, the resin-bound material is aminolysed with a PEG-based diamine as described above, to yield:

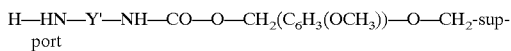

Acylation/Activation/Aminolysis Steps

One acylation/activation/aminolysis cycle would yield:

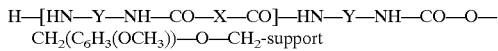

and so forth, repeating the three step acylation/activation/aminolysis cycle until the linker was of the desired length. This yields a linker of Formula (III):

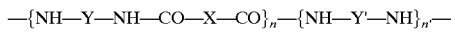

where n' is 1, and a product of Formula (IV):

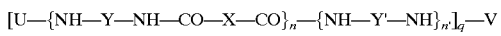

where U is H and V is —Z—Q-support.

In the case of a hydroxyl resin, cleavage from the resin would form a product of Formula (IV) where U and V are H, through decarboxylation of the terminal carbamic acid:

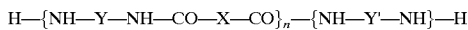

In the case of an amino resin, cleavage from the resin would form a product of Formula (IV) where U is H and V is CONH$_2$:

H—{NH—Y—NH—CO—X—CO}$_n$—{NH—Y'—NH}—CONH$_2$

V may also be considered to be H, attached through a divalent linker —CONH—.

The acylation/activation/aminolysis cycles described in Schemes I-A and I-B may be repeated many times using the same or different diacids and diamines. Since the oligomerization is performed rationally, one step at a time, there is an opportunity to vary the diamine and the diacid component at any stage (e.g., using a different diacid where X is —(CH$_2$)$_4$— instead of —(CH$_2$)$_2$—) and thus tailor hydrophobicity and length.

Once the desired number of cycles has been performed to achieve the desired linker length, the chain may then be extended (with a peptide, for example) using standard techniques of solid phase synthesis.

An automated peptide synthesizer can be programmed to perform the steps. Once the desired chain is assembled, a peptide can be synthesized on the terminal amino group. Since no protection groups are used in the construction of the chain, this chain extension may be performed using standard Boc (tert-butyloxycarbonyl) or Fmoc (fluorenylmethoxycarbonyl) techniques prior to cleavage from the resin in the standard way (Fields, supra). Alternatively, the terminal groups can be modified with an aminooxyacetyl group or an aldehyde precursor by standard techniques (Rose, *J. Am. Chem. Soc.* 116:20 (1994)) either prior to cleavage from the resin or afterwards. The PEG-based chain contains ether and amide bonds, both of which are compatible with general peptide deprotection and cleavage techniques, including liquid hydrogen fluoride ("HF").

Products, after cleavage from the resin and purification by standard techniques of peptide chemistry, have Formula (IV):

[U—{NH—Y—NH—CO—X—CO}$_n$—{NH—Y'—NH}$_{n'}$]$_q$—V and contain a water soluble organic polyamide-based chain having a precise number of repeating units of Formula (III):

—{NH—Y—NH—CO—X—CO}$_n$—{NH—Y'—NH}$_{n'}$—

It should be noted that the acylation step and the activation step of the cycle of the present invention is similar to the acylation step of conventional solid phase peptide synthesis cycles and does not disturb the usual protecting groups whether they be Boc-, Fmoc-, butyl- or benzyl-based that may be present on substituents in the linker or product. However, the aminolysis step involves an excess of a primary amine and so causes loss of Fmoc protection from amino groups and of formyl protection from tryptophan, and this should be taken into account when planning a synthesis.

Another synthesis reaction of the present invention involves two steps: acylation and aminolysis. By using an excess of a doubly activated diacid in the acylation step, it is not necessary to activate the free acid group prior to the aminolysis step, as shown in Scheme II.

SCHEME II

Acylation Step

In the case where a diactivated diacid (such as the acyl chloride or active ester, represented by "L" where L is a leaving group) is used to acylate the amino groups attached to a resin suitable for solid phase peptide synthesis (NH$_2$—Q-support or HO—Q-support):

NH$_2$—Q-support+L—CO—X—CO—L (excess)→L—CO—X—CO—NH—Q-support or

HO—Q-support+L—CO—X—CO—L (excess)→L—CO—X—CO—O—Q-support

It is important to use an excess of acylating reagent over the amino groups present to avoid favoring a "bridging" side reaction, whereby the same divalent diacid derivative acylates two amino groups. Such bridged species cannot participate in aminolysis and chain extension and represent loss of yield and presence of impurities which must be removed after cleavage of product from the support.

A particular special case is when the diacid is carbonic acid. Carbonyldiimidazole is a suitable diactivated form of this diacid. Its use yields imidazolyl-CO—NH—Q-support and imidazolyl-CO—O—Q-support, respectively.

Aminolysis Step

The aminolysis step involves addition of a diamine of Formula (I), NH$_2$—Y—NH$_2$, of homogeneous length:

NH$_2$—Y—NH$_2$+L—CO—X—CONH—Q-support→NH$_2$—Y—NH—CO—X—CONH—Q-support

The acylation and aminolysis steps may then be repeated several times as described above in Scheme I.

It is important that a sufficient amount of reagent solution be used in each of the reaction steps of Schemes I and II, to enable the resin to form a slurry. Since the resin swells greatly as the number of cycles increases, it is preferable to use absolute concentrations that are similar to those described in the Schemes above and adjust the volumes accordingly. In addition, it is preferable to use more than 8 milliliters of solution for syntheses of longer chains when starting with about 0.3 mmoles of resin. The degree of swelling depends upon the type of support or resin used (composition, degree of cross-linking, etc.), along with being substitution dependent (i.e., how many mmol/g) as well as length dependent. Accordingly, insufficient liquid (solution) may lead to less than quantitative coupling. While the acylation step is easily monitored by the Kaiser test, the activation step is relatively difficult to follow. When the activation step is incomplete at one cycle, activation may nevertheless occur during a subsequent cycle, thus leading to a deletion where the product may be missing a repeat unit —(CO—X—CO—NH—Y—NH)—. Use of excess reagents will eliminate this problem. The term "excess" is intended to mean a molar excess of the diacid (or derivative), the activating agent and the diamine reagent: for the diacid, activating agent and diamine, respectively, preferably between about 3–20 fold, 10–40 fold, 20–200 fold; more preferably between about 4–15 fold, 15–30 fold, 40–180 fold; most preferably between about 5–14 fold, 20–28 fold, 50–150 fold molar excess.

There are numerous resins that are suitable for solid phase peptide synthesis, and thus well suited to the synthesis schemes of the present invention. These resins can be obtained commercially or synthesized through standard techniques, and include, for example, tert-butoxycarbonyl-Leu-O—CH$_2$-phenyl(acetamido) resin ("Boc-Leu-PAM" resin, Bachem, Bubendorf, Switzerland), 9-fluorenylmethoxycarbonyl-cysteamine-Sasrin resin ("Fmoc"-cysteamine-Sasrin resin, Bachem), Fmoc-aminobutyric acid-Sasrin resin (Bachem), Fmoc-Lys(4-methyltrityl)-methylbenzhydrylamine resin ("Fmoc-Lys(Mtt)-MBHA" resin), and such. Any of the aforementioned resins may be amino-deprotected and used for acylation with a diacid derivative.

Similarly, a hydroxyl resin such as Sasrin (Bachem), Wang or PAM can be acylated directly with a diacid derivative. Alternatively, a hydroxyl resin such as Sasrin (Bachem), Wang or PAM can be activated by CDI to give im-CO—O—CH$_2$-linker-resin, noting that in the case of Sasrin this gives im-CO—O—CH$_2$—(C$_6$H$_3$(OCH$_3$))—O—CH$_2$-resin. See Bethel, et al., *J. Biol. Chem.* 254:2572–2574 (1979). Such an activated hydroxyl resin may be aminolysed with a diamine to give NH$_2$—Y—NH—CO—O—Q-support as described by Bethel et al., supra.

In the case of orthogonally protected diamino resins such as Fmoc-Lys(Mtt)-MBHA-resin, normally only one amino group is deprotected prior to acylation. Otherwise, a diacid derivative such as SA may be coupled directly to a resin such as Sasrin to give a resin with a free carboxyl group which may be used for activation. The resin, once amino-deprotected, is illustrated by the formula NH$_2$—Q-support, where Q is a bivalent organic radical, for example CH(R')—CO— (where R' is an amino acid side chain as in the case of deprotected Boc-Leu-), —CH$_2$—CH$_2$S— (in the case of deprotected Fmoc-cysteamine), —CH$_2$—CH$_2$—CH$_2$CO— (in the case of deprotected Fmoc-aminobutyric acid), —CH(CH$_2$—CH$_2$—CH$_2$—CH$_2$NH—Mtt)CO— (in the case of Fmoc-deprotected Fmoc-Lys(Mtt)), or may represent a side chain-protected polypeptide in which case the NH$_2$ group of NH$_2$—Q-support is taken to mean the free amino group of the polypeptide previously synthesized on the support. NH$_2$—Q-support may also be taken to represent an MBHA resin. Where the resin is illustrated by the formula HO—Q-support, Q is a linker group designed to liberate a terminal carboxyl group from the acylated (ester-linked) chain upon cleavage of the chain from the resin. Such groups are well known (*Methods in Enzymology* Vol. 289) and are incorporated into the PAM resins and Sasrin resins which are commercially available from Bachem and other suppliers. Products are then cleaved from the resin using a standard technique appropriate for the particular resin used. The support can be for example the polystyrene resin of commercial PAM, Sasrin or MBHA resins, or other similar supports used for solid phase peptide synthesis and mentioned in *Methods in Enzymology* Vol. 289. However, other materials and configurations of support are also contemplated.

In another embodiment of the invention, it has been found that once an activated resin is aminolysed with a diamine to give NH$_2$—Y—NH—CO—X—CO—O—Q-support, the free amino group may then be acylated with a derivative of a diacid and the polyamide elongation process can proceed for many cycles to give good yields of desired product. This is in contrast to the expectation that certain side reactions, such as the bridging of two activated groups by the diamine, would quickly render the technique unpractical. After cleavage from the resin by standard techniques, the polyamide is liberated with a terminal amino group, which may be exploited for functionalization (e.g. creation of symmetrical molecules).

As noted above, the polyamide-based chains of the invention are useful for modifying target molecules or materials such as surfaces. These chains can be coupled to residues of macromolecules, e.g. amino acid residues of polypeptides, without drastically altering the charge present on the residue or without introducing groups at locations likely to interfere with the binding properties of the macromolecules, and are attached through linkages that are stable under a variety of conditions, particularly physiologically relevant conditions.

Particularly suitable means of attaching the PEG-based chains of the present invention to polypeptides and proteins involve attachment through hydrazone and oxime chemistry at the amino and carboxy termini of the polypeptide chains as taught in Rose, et al., European Patent 0243929, incorporated herein by reference.

According to a preferred embodiment of the present invention, protein and other organic target molecules may be chemically modified by conjugation to the precise length water soluble organic polymer-based chains of the invention such as the PEG-based chains described herein. The production of such protein conjugates is of interest because of the desirable properties conferred by the attachment of the water soluble polymers. These desirable properties include increased solubility in aqueous solutions, increased stability during storage, reduced immunogenicity, increased resistance to enzymatic degradation, compatibility with a wider variety of drug administration systems, and increased in vivo half-life. These properties that are brought about by the modification of polypeptides with PEG or other water soluble polymers are especially of interest when the polypeptide is to be used as a therapeutic agent injected into the body or when the polypeptide is to be used in a non-medical application such as in assays, usually immunoassays, for the detection and/or quantification of a compound of interest.

A "modified" target molecule or material is a molecule or material that has been modified by conjugation to one or more polyamide-based chain(s) of the invention. A "homogeneous" modified composition of the invention refers to a chemical composition in which substantially all of the modified target molecules or materials have essentially the same polyamide-based chains, i.e., a range in the molecular weight of the attached polymer(s) does not exist. For example, a PEG-based chain of the invention can have the —(CH$_2$CH$_2$O)$_p$— group present in either the X, the Y or both substituents of Formula (III), resulting in a formula of

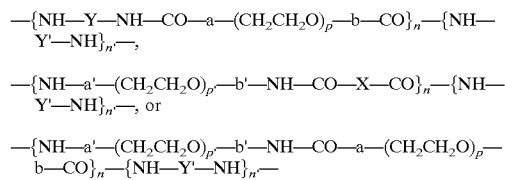

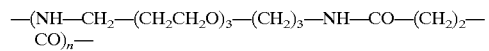

One such exemplary chain has the following PEG-based formula:

—(NH—CH$_2$—(CH$_2$CH$_2$O)$_3$—(CH$_2$)$_3$—NH—CO—(CH$_2$)$_2$—CO)$_n$—

The PEG-based chains present in a homogeneous composition will all have the same p or p' integer values and the composition will be essentially exempt of homologous PEG-based chains having a different p or p' value. It is important to understand that reference is to a constant p or p' value within a given monomer unit such as —{NH—Y—NH—CO—a—(CH$_2$CH$_2$O)$_p$—b—CO}$_n$—{NH—Y'—NH}$_{p'}$— or —(NH—a'—(CH$_2$CH$_2$O)$_{p'}$—b'—NH—CO—X—CO)—. It is also possible to select a monomer unit with a different p or p' value at different cycles, and indeed, it is also possible to vary a, a', b, b', p, p' and X at each cycle of the synthesis and still obtain a homogeneous composition.

The polyamide-based chains of the invention are attached to the target molecule by covalent conjugation, for example, by an oxime linkage. "Covalently conjugated" or "conjugated" refers to the attachment of a polyamide-based chain to the target molecule by standard techniques of bioconjugate chemistry (*Bioconjugaie Techniques*, supra), and especially through the N- and C-terminal labeling techniques described in Rose, et al., European Patent 0243929. For example, a PEG-based chain can contain a terminal aminooxyacetyl ($NH_2OCH_2CO-$) group which reacts with an aldehyde group on the protein to form an oxime bond, or it can contain a glyoxylyl ($O=CHCO-$) group which reacts with an aminooxy group on the protein (introduced for example by alkylation of a thiol with $BrCH_2CO-NHCH_2CH_2NHCOCH_2ONH_2$ as described by Werlen, et al., *Cancer Research* 56:809–815 (1996)), or it can contain a bromoacetyl group which alkylates a thiol on the protein. Alternatively, conjugation between the PEG-based chain and the target molecule can be by activation (e.g. with a diimide and N-hydroxysuccinimide) of a terminal carboxyl group on the chain (for example, where V is —OH and n' is 0) and acylation of amino groups (such as lysine side chains) on the target molecule, or conjugation may be effected by activation of carboxyl groups on the target molecule (e.g. with water soluble carbodiimide) followed by addition of a PEG-based chain having a free amino group (for example, where U is H).

If the modified molecule is to be used for antigenic or immunogenic purposes, it is apparent to one skilled in the art that any spacer groups used should not be strongly immunogenic. Where the conjugated polymer is to be used for binding purposes, any spacer group should enhance or at least not interfere with properties such as binding, avidity, product stability or solubility.

The present invention provides a process for preparing proteins modified with one or more polyethylene glycol-based chains of precise length. More specifically, methods and compounds are described for modifying, under mild conditions, a macromolecule target, such as a protein, peptide, other organic compound such as a plastic, or a surface containing macromolecules, with one or more polyethylene glycol-based chains of precise length.

A preferred method of conjugation is based upon standard chemistry, which is performed in the following manner. The PEG-based chain has an aminooxyacetyl group attached during synthesis (for example by acylation with activated Boc-aminooxyacetic acid), protection is removed, and the PEG-based chain is cleaved from the resin, purified and characterized using the standard techniques of solid phase peptide synthesis (*Methods in Enzymology* Vol. 289 and the Examples). The target molecule has a terminal serine or threonine residue, which is oxidized to a glyoxylyl group under mild conditions with periodate according to Rose, *J. Am. Chem. Soc.* 116:30–33 (1994) and European Patent 0243929. The aminooxy component and the aldehyde component are mixed in approximately equal proportions at a concentration of 1–10 mM in aqueous solution at mildly acid pH (2 to 5) at room temperature and the conjugation reaction (oximation) followed by reversed phase high pressure liquid chromatography (HPLC) and electrospray ionization mass spectrometry (ES-MS). The reaction speed depends on concentrations, pH and steric factors but is normally at equilibrium within a few hours, and the equilibrium is greatly in favor of conjugate (Rose, et al., *Bioconjugate Chemistry* 7:552–556 (1996)). A slight excess (up to five fold) of one component forces the conjugation reaction towards completion. Products are isolated and characterized as previously described for oximes. Peptides and small proteins (e.g. insulin) may be purified by reversed phase HPLC (Rose, *J. Am. Chem. Soc.*, supra and Rose, et al., *Bioconjugate Chemistry*, supra) whereas larger proteins (e.g. antibodies and their fragments) are best purified by ion-exchange chromatography, or by gel filtration techniques as for the trioxime described by Werlen, et al., *Cancer Research* 56:809–815 (1996).

Another method of conjugation is performed in the following manner. The PEG-based chain is synthesized on the Sasrin resin from Bachem. Using the procedure recommended by the resin manufacturer (Bachem), the chain is cleaved from the resin by repeated treatment with 1% TFA in dichloromethane and the solution of cleaved chain is neutralized with pyridine in methanol. After evaporation of solvents at room temperature (no heat is applied) and purification of the cleaved chain as if it were a polypeptide, the carboxyl group which was connected to the resin is activated (e.g. with HATU) and coupled to a nucleophilic group (such as an amino group) on the target molecule (or surface) by standard techniques of peptide chemistry.

If desired, the modified target molecule or material can be purified from the reaction mixture by one of numerous purification methods that are well known to those of ordinary skill in the art such as size exclusion chromatography, hydrophobic interaction chromatography, ion exchange chromatography, preparative isoelectric focusing, etc. General methods and principles for macromolecule purification, particularly protein purification, can be found, for example, in "Protein Purification: Principles and Practice" by Scopes, 2nd ed., Springer-Verlag, New York, N.Y., (1987), which is incorporated herein by reference.

As noted above, the PEG-based linkers of the subject invention find particular utility in enhancing the properties of target molecules or materials. For example, the advantages of coupling water soluble polymers, especially polyethylene glycol, to proteins have been well documented and include increased solubility of the modified protein as compared with the native protein at physiological pH when the native protein is insoluble or only partially soluble at physiological pH, a decrease in the immune response generated by the native protein, an increased pharmacokinetic profile, an increased shelf-life, and an increased biological half-life. In more general terms, an important advantage of the subject invention, particularly in the case of biologically important target macromolecules such as polypeptides, is that the macromolecule can be modified by the attachment of the PEG or water soluble polymer-based linkers without substantially reducing or interfering with the biological activity of the macromolecule. The term "biological activity" includes enzymatic activity, the ability to bind to receptors (including antibodies), the ability to bind ligands, the ability to induce an immune response, the ability to produce a therapeutic effect, and the like.

A further advantage of the subject invention is that macromolecules, e.g. polypeptides, modified by the precise length PEG-based chains of the invention are essentially homogeneous compounds, unlike those made by joining several varied length water soluble polymers, for example polymers containing a —$(CH_2CH_2O)_m$— group, where the value of m varies greatly among the polymers. Thus, the subject invention provides for modified targets that possess the advantages associated with the conjugation of water soluble polymers while minimizing the loss of homogeneity associated with the modification. Homogeneity is most important for biopharmaceuticals, to reduce lot-to-lot variations and to facilitate product development, characterization, interpretation of results (of a homogeneous compound rather than of a mixture) and obtaining regulatory approval.

Polypeptides of interest include monoclonal and polyclonal antibodies; hormones; cytokines, including colony stimulating factors such as M-CSF, GM-CSF and G-CSF;

stem-cell growth factor; lymphokines; IL-2 and IL-3; growth factors, including, PDGF, EGF; peptide hormones, including hGH and erythropoietin; blood clotting factors, including Factor VIII; immunogens; enzymes and enzyme inhibitors; ligands; vaccine antigens, and the like. Polypeptides of interest may be isolated from their natural sources, genetically engineered cells, or produced by various in vitro synthesis methods. The following patent applications (which are hereby incorporated by reference) report PEG-based modifications of various biologically important proteins: U.S. Pat. Nos. 4,179,337; 4,609,546; 4,261,973; 4,055,635; 3,960,830; 4,415,665; 4,412,989; 4,002,531; 4,414,147; 3,788,948; 4,732,863; and 4,745,180; EP No. 152,847; EP98110 published Jan. 11, 1984; and JP5792435. These proteins, in their unmodified state, are target macromolecules for modification, as described herein.

The terms "peptide", "polypeptide" and "protein" are used interchangeably herein and are intended to mean both naturally occurring and recombinant forms, as well as other non-naturally occurring forms of the peptide or protein which are sufficiently identical to the naturally occurring peptide or protein to allow possession of similar biological or chemical activity.

Although the chains of the instant invention can be referred to as "linkers", the invention contemplates using these chains where the target molecule is not necessarily linked to another molecule. Accordingly, a single target macromolecule may be attached to a single chain of Formula (III) to give a product of Formula (IV), where q is 1:

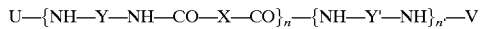

such that U (or V) is the target molecule and V (or U) is a terminal group. In another embodiment of the invention, a single target molecule has several chains of Formula (III) attached to it at various positions.

In using the chain of the invention in the function of a linker, two target molecules, which may be the same or different, are attached to a single chain of Formula (III), such that in the product of Formula (IV) the groups U and V are the same or different, but are both target macromolecules. This latter embodiment can be referred to as having a "dumbbell" construction.

Accordingly, in another embodiment of the present invention are provided target molecules modified by a PEG-based chain of the invention. These are referred to herein as "polymer conjugates". As discussed above, preferably the target molecule is a polypeptide, more preferably a polypeptide of biological importance.

The invention also contemplates individual target molecules that are modified by one or more different PEG-based chains of the invention by means of reaction with different embodiments of the PEG-based chains. In addition, individual target molecules can be modified with multiple PEG-based chains at a single site on the target molecule.

It is of particular interest to use the PEG-based linkers of the invention to modify polypeptides for use as drugs and for use in assays. Polypeptides for use in assays include specific binding proteins, polypeptides recognized by specific-binding proteins, and enzymes. By specific-binding proteins it is intended antibodies, hormone receptors, lectins, and the like. The term "antibodies" is intended to include both polyclonal and monoclonal antibodies with natural immunoglobulin sequences, synthetic antibody derivatives, and the like. Further, the antibodies may be modified so as to be joined to any of a variety of labels, fluorescent, radioactive, enzymatic, biotin/avidin or the like. Synthetic antibody derivatives include natural immunoglobulin sequences that have been mutated and selected for altered binding specificity, various immunoglobulin gene derived polypeptides, typically single chain, produced by genetically modified bacteria, antibodies modified so as to contain modified constant regions and the like; a review of such synthetic antibody derivatives based on the principles of antibody formation is provided in Winter, et al., *Nature*, 349:293–299 (1991). An antibody is a glycoprotein of the globulin type that is formed in an animal organism in response to the administration of an antigen and that is capable of combining specifically with the antigen. These are also referred to as immunoglobulins. Antibody fragments can retain some ability to selectively bind with their antigen or hapten. The ability to bind with an antigen or hapten is determined by antigen-binding assays (see, for example, Antibodies: A Laboratory Manual, Harlow and Lane, eds., Cold Spring Harbor, N.Y. (1988), which is incorporated herein by reference). Such antibody fragments include, but are not limited to, Fab, Fab' and (Fab')$_2$. A native antibody is one which is isolated from an animal or from an animal or hybrid animal (hybridoma) cell line.

Target macromolecule polypeptides can also be produced by a prokaryotic microorganism or a eukaryotic cell that has been transformed with a native or modified polypeptide-encoding DNA sequence, preferably of human origin. Target polypeptides may also be identified by phage library techniques and then synthesized chemically, as in the Examples. Variants of naturally occurring p6lypeptides, wherein substantial identity of amino acid sequences has been maintained (i.e., the sequences are identical or differ by one or more amino acid alterations (deletions, additions, substitutions) that do not cause a substantially adverse functional dissimilarity between the mutationally altered protein and native protein) are useful herein.

Salts of any of the target molecules described herein, e.g., polypeptides, water soluble polymers and derivatives thereof, will naturally occur when such molecules are present in (or isolated from) aqueous solutions of various pHs. All salts of peptides and other macromolecules having the indicated biological activity are considered to be within the scope of the present invention. Examples include alkali, alkaline earth, and other metal salts of carboxylic acid residues, acid addition salts (e.g., HCl) of amino residues, and zwitterions formed by reactions between carboxylic acid and amino residues within the same molecule.

As noted above, the target molecule can be a nucleic acid, including by way of illustration and not limitation, nucleotides, oligonucleotides, and linear or circularized, single or double-stranded DNA and RNA. In order to enhance the properties of nucleic acids, such as enhancing mobility under assay conditions, it is often desirable to introduce a polymer chain to the nucleic acid. This has been shown to be successful using ethylene-oxide-based linkers (see for example, Grossman, et al., U.S. Pat. No. 5,777,096). Accordingly, it is expected that nucleic acids modified with the PEG-based chain of precise length of this invention will have similar enhanced properties.

The target molecule can also be a liposome. Liposomes have many uses but are of particular interest as carriers for drug delivery. In order to enhance the properties of liposomes, it is often desirable to introduce a functional compound such as a protein, peptide, etc. to the liposome surface. Since this has been accomplished using other PEG-based linkers (see for example, Tagawa, et al., U.S. Pat. No. 5,556,948), it is expected that a liposome modified with the PEG-based chain of precise length of this invention will have similar enhanced properties.

In addition, the PEG-based chains of the invention can also be attached to a matrix or a solid phase, such as by way of illustration and not limitation, the surface of a silicon or sensor chip or a gold or glass or other biosensor surface, a tissue culture plate, cell or membrane, or a synthetic or natural resin. One can chemoselectively ligate a PEG-based chain to a solid phase through the use of complementary functional groups introduced to the solid phase. Such solid phases can readily be dipped in alternating baths of a diamine of Formula (I) and a derivative of a diacid of Formula (II), with activation and wash baths in between, to attach the PEG-based chains of the invention to its surface.

When a target molecule is therapeutically effective for human and veterinary uses, such as cancer therapy and the treatment of infectious diseases, the modified target molecule, once produced and purified, may be incorporated into a pharmaceutical composition for the same uses.

A therapeutic agent is any molecule, which, when administered to an animal, prevents or alleviates a disease or arrests or alleviates a disease state in the animal. Therapeutic agents may include, but are not limited to, antitumor antibiotics, antiviral proteins, radioisotopes, pharmaceuticals or a toxin. It is expected that therapeutic agents, modified with the polyamide-based chains described herein, will have the same or similar biological activity as the unmodified agent but with the improvements in properties discussed above.

The modified therapeutic agent can be formulated in a nontoxic, inert, pharmaceutically acceptable aqueous carrier medium. A "pharmaceutically acceptable carrier" means any of the standard pharmaceutical carriers, such as a phosphate buffered saline solution; water; or emulsion, such as an oil/water emulsion; potentially including various types of wetting agents. The modified therapeutic agent can be formulated in a nontoxic, inert, pharmaceutically acceptable aqueous carrier medium, preferably at a pH ranging from 3 to 8, more preferably ranging from 6 to 8. When used for in vivo therapy, the sterile modified therapeutic agent composition will comprise the modified protein dissolved in an aqueous buffer having an acceptable pH upon reconstitution. The modified therapeutic agent can be formulated with a number of excipients such as amino acids, polymers, polyols, sugar, buffers, preservatives, other a proteins, etc. Specific examples include: octylphenoxy polyethoxy ethanol compounds; polyethylene glycol monostearate compounds; polyoxyethylene sorbitan fatty acid esters; sucrose; fructose; dextrose; maltose; glucose; dextran; mannitol; sorbitol; inositol; galactitol; xylitol; lactose; trehalose; bovine or human serum albumin; citrate; acetate; Ringer's and Hank's solutions; saline; phosphate; cysteine; arginine; carnitine; alanine; glycine; lysine; valine; leucine; polyvinylpyrrolidone; polyethylene glycol; etc. Preferably this formulation is stable for at least 6 months at 4° C.

As a composition, the modified therapeutic agent can be administered to the subject by methods known in the art, where "administered" means providing the subject with an effective amount of the compound or pharmaceutical composition. Methods of administration include, but are not limited to, oral, intravenous, transdermal, and parenteral administration. Administration may be effected continuously or intermittently throughout the course of other treatments. Methods of determining the most effective means and dosage of administration are well known to those of skill in the art and will vary with the compound or composition for treatment, the purpose of therapy and the animal or patient being treated. This composition may contain other compounds that increase the effectiveness or promote the desirable qualities of the particular target molecule. The composition must be safe for administration via the route that is chosen, sterile and effective. To maintain the sterility and to increase the stability of the modified therapeutic agent, the composition can be lyophilized and reconstituted prior to use.

Preferably, the formulation is suitable for parenteral administration to humans or animals in therapeutically effective amounts. These amounts may be determined by the in vivo efficacy data obtained after preclinical testing using animal models of the disease state of interest or in vitro assays generally accepted as correlating with in vivo efficacy.

It is also of interest to supply the polyamide-based chains of the invention in the form of a kit, so as to provide for the convenient and reproducible modification of target molecules of interest. Kits of interest may contain solutions comprising the polyamide-based chains of the invention, buffers, reaction indicator compounds, instruction, protein concentration measurement reagents, e.g., for Bradford assays, and the like. Reagent solutions will preferably be supplied in premeasured amounts. Alternately, the kits may contain a solution comprising a diacid as a derivative and a solution comprising a diamine for synthesis of the polyamide-based chains, along with the materials noted above. The kits may also contain the target molecule whose properties are being modified or enhanced.

Kits can contain a series of individual solutions (or powdered form) polyamide-based chains of known composition, molecular weight and configuration (whether mono-polymer, bi-polymer or multi-polymer) attached to target molecules of known molecular weight and composition that can be used as standards, for example to estimate completion and/or yield of conjugation reactions or to provide molecular weight standards.

One preferred kit, useful for synthesizing a water soluble organic polyamide-based chain having a precise number of repeating units, said chain having the formula:

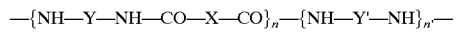

where: n is an integer from 1–100; n' is 0 or 1; X and Y are divalent organic radicals lacking reactive functional groups or are absent and are the same or different, and can vary independently with each of said repeating units; Y' is a divalent organic radical lacking reactive functional groups or is absent; comprising: (a) Z—Q-support, where Z is H$_2$N— or HO—; Q is a linker or a target molecule; and the support is a solid phase, matrix or surface; (b) a diacid having the formula, HOOC—X—COOH or a derivative thereof; and (c) a diamine having the formula, NH$_2$—Y—NH$_2$.

Another exemplary kit of the invention is also useful for enhancing or modifying a target molecule, and comprises: (a) reagents for synthesizing a water soluble organic polyamide-based chain having a precise number of repeating units, said chain having the formula:

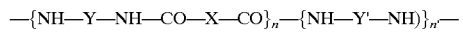

where: n is an integer from 1–100; n' is 0 or 1; X and Y are divalent organic radicals lacking reactive functional groups or are absent and are the same or different, and can vary independently with each of said repeating units; and Y' is a divalent organic radical lacking reactive functional groups or is absent; comprising: (i) Z—Q-support, where Z is H$_2$N— or HO—; Q is a linker or a target molecule; and the support is a solid phase, matrix or surface; (ii) a diacid having the formula, HOOC—X—COOH, or a derivative thereof, where X is a divalent organic radical lacking reactive functional groups or is absent; and (iii) a diamine having the formula, $NH_2$—Y—$NH_2$, where Y is a divalent organic radical lacking reactive functional groups or is absent; and (b) a target molecule whose properties are being modified or enhanced, and having an optional divalent spacer or linker.

The aforementioned kits can further comprise one or more of the following: at least one additional diacid having the formula, HOOC—X—COOH, wherein the X substituent is different from the X substituent in the first diacid, or a derivative thereof; at least one additional diamine having the formula, $NH_2$—Y—$NH_2$, wherein the Y substituent is different from the Y substituent in the first diamine; and an activating agent selected from the group consisting of carbonyl diimidazole, disuccinimidyl carbonate and O-(7-azabenzotriazol-1-yl)-1,1,3,3-tetramethyluronium hexafluorophosphate.

Another embodiment of the invention is a kit, useful for enhancing or modifying a target molecule, which comprises: (a) a water soluble organic polyamide-based chain having a precise number of repeating units, said chain having the formula:

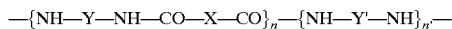
—{NH—Y—NH—CO—X—CO}$_n$—{NH—Y'—NH}$_{n'}$— wherein: n is an integer from 1–100; n' is 0 or 1; X and Y are divalent organic radicals lacking reactive functional groups or are absent and are the same or different, and can vary independently with each of said repeating units; and Y' is a divalent organic radical lacking reactive functional groups or is absent; and (b) a target molecule whose properties are being modified or enhanced, and having an optional divalent spacer or linker.

Modified target molecules or materials of the invention can be used in improved kits for diagnostic purposes or as improved reagents for assays, for example, in binding assays such as immunoassays. For example, modified target molecule compositions bearing antigen peptides provide increased detection sensitivity in solid-phase immunoassays. The larger, bi-valent or multivalent modified materials can more readily adhere to surfaces such as the multiwell plates used in immunoassays. Multivalent species can have much-enhanced binding avidities (e.g., Terskikh, et al., supra), and PEG-based chains can be used to assemble synthetic multivalent constructions (see Examples). Modified target molecules, particularly multi-PEG-based chain-containing target molecules, find use in in vitro assays that use a signal amplification step for detection of an analyte, as for example in a branched DNA based assay. Amplification is achieved by the attachment of multiple PEG-based chains (rather than a single PEG-based chain) to a single analyte molecule, wherein a reporter group attached to each PEG-based chain contributes to a detectable signal in a subsequent assay step. Therapeutic agents which increase hematocrit may be made by connecting two erythropoietin mimetic peptides through PEG-based polyamide linkers of the invention (Examples 11 and 12).

The present invention provides further in vitro use of PEG-based chains. A PEG-based chain can be used to "tag" a target molecule and thus enable the molecule's subsequent detection and or quantitation in a number of ways. Most simply, the attached PEG-based chain allows one to perform a simple size separation that will separate the PEG-based chain tagged-target molecule from other molecules in a mixture. It is now readily apparent that different physicochemical properties of organic polymers can be taken advantage of in this way simply by changing the polymer. For example, a slightly hydrophobic PEG-based chain would allow separation based on hydrophobicity, or one can use a polymer binding column that then selects for or against the PEG-based chain as desired. In addition the PEG-based chain can be chosen, or modified, so that it can be directly detected. This imparts the advantage that the PEG-based chain may contain multiple detectable sites (or repeating units), such that each site present in the polymer binds or is recognized by a detection system, thus resulting in the amplification of detection signal.

EXAMPLES

Abbreviations

| | |
|---|---|
| Abu | aminobutyric acid |
| amu | atomic mass units |
| AoA | aminooxyacetyl |
| Boc | tert-butoxycarbonyl |
| 2BrZ | 2-bromobenzyloxycarbonyl |
| Bzl | benzyl |
| CDI | carbonyldiimidazole |
| DAH | 1,6-diaminohexane, $H_2N$—$(CH_2)_6$—$NH_2$ |
| 'DAH' | a residue of DAH |
| DCM | dichloromethane |
| DIEA | diisopropylethyleamine |
| DMAP | 4-dimethylaminopyridine |
| DMF | dimethylformamide |
| EMP | erythropoietin mimetic peptide |
| EPO | erythropoietin |
| Fmoc | 9-fluorenylmethoxycarbonyl |
| HATU | O-(7-azabenzotriazol-1-yl)-1,1,3,3-tetramethyluronium hexafluorophosphate |
| HF | hydrogen fluoride |
| HOBT | N-hydroxybenzotriazole |
| MALDI-TOF | matrix-assisted laser desorption ionization time of flight |
| MBHA | methylbenzhydrylamine |
| Mtt | 4-methyltrityl |
| NMP | N-methylpyrrolidone |
| OSu | the N-hydroxysuccinimide ester of a carboxylic acid or of the Fmoc protecting group |
| PAM | phenyl(acetamido)methyl, i.e., strictly —$C_6H_4CH_2CONHCH_2C_6H_4$— (polystyrene), e.g., Boc-Leu-OCH$_2$-PAM |
| PEG | polyethylene glycol, oligomers of —$CH_2CH_2O$— |
| 'PEG' | —NH—$CH_2CH_2CH_2$—$(OCH_2CH_2)_3$—$CH_2NH$— which is a residue of the PEG-based diamine, $NH_2CH_2CH_2CH_2$—$(OCH_2CH_2)_3$—$CH_2NH_2$ |
| SA | $C_4H_4O_3$, succinic anhydride |
| succ | —$COCH_2CH_2CO$—, a residue of succinic acid |
| t-Bu | tert-butyl |
| TFA | trifluoroacetic acid |
| TFMSA | trifluoromethanesulphonic acid |

EXAMPLE 1

Synthesis of H-('PEG'-succ)$_3$-Leu-PAM Resin

Three cycles of -'PEG'-succ- were performed on a H-Leu-PAM resin (Bachem) to yield:

H—[NHCH$_2$CH$_2$CH$_2$—(OCH$_2$CH$_2$)$_3$—CH$_2$NH—CO—CH$_2$CH$_2$CO]$_3$-Leu-PAM resin 0.5 g (approximately 0.3 mmol) Boc-Leu-PAM resin (Bachem, Switzerland) was swollen in DMF and deprotected with TFA on an ABI 430A peptide synthesizer. The TFA was drained and the resin washed with DMF in the normal way. This produced H-Leu-PAM resin (as its TFA salt) ready for acylation. Sometimes such products are written H-Leu-OCH$_2$-PAM resin and sometimes H-Leu-PAM resin but both designations refer to standard PAM peptide synthesis resin.

ince "Leu" is a residue of leucine (—NH—CH($C_4H_9$)—CO—), the product is correctly written "H-Leu-PAM" resin, although "Leu-PAM" is often used. In a similar way and as noted in the abbreviations section, 'PEG' is a residue (—NHCH$_2$CH$_2$CH$_2$—(OCH$_2$CH$_2$)$_3$—CH$_2$NH—) and similarly, when terminal, the terminal group (here a hydrogen) should be shown.

Acylation: H-Leu-PAM resin prepared as above was swollen in DMF, drained and acylated with 4 mmole SA by vortex mixing at room temperature for 30 minutes. SA was dissolved in 8 ml DMF (Burdick and Jackson High Purity grade) which is 0.5 M in HOBT (Fluka) and to which 400 µl DIEA was added. After draining and washing the resin with DMF, the Kaiser ninhydrin test established that acylation was complete.

Activation: The free carboxyl group was activated with 8 mmole of CDI (Fluka) in 8 ml DMF for 30 minutes.

Aminolysis: After a brief drain and wash with DMF, the resin-bound imidazolide was aminolysed with the 'PEG'-based diamine, NH$_2$CH$_2$CH$_2$CH$_2$—(OCH$_2$CH$_2$)$_3$—CH$_2$NH$_2$, (4 ml diamine premixed with 4 ml DMF which is 0.5 M in HOBT) for 60 minutes. After thorough washing with DMF, the Kaiser test showed the characteristic blue color and the amino resin was ready for the next acylation/activation/aminolysis cycle.

The acylation, activation and aminolysis cycle was repeated two more times to yield H-('PEG'-succ)$_3$-Leu-PAM resin. The product was characterized by further chain extension followed by cleavage as described in Example 2.

EXAMPLE 2

Synthesis of H-Tyr-('PEG'-succ)$_3$-Leu-OH

The resin-bound amino group of the third 'PEG' of the H-('PEG'-succ)$_3$-Leu-PAM resin from Example 1, was acylated with Boc-Tyr(2BrZ) on the ABI 430A using standard HBTU activation and DIEA as base, then the resin was treated for deprotection/cleavage in the normal way (TFA to remove Boc, HF for 60 min at 0° C. in the presence of 5% para-cresol to remove benzyl-based side chain protection 2BrZ and cleave from the resin). After evaporation of HF, para-cresol was extracted with −20° C. diethylether. The resulting cake of resin and product was taken up in 50% acetonitrile and the resin filtered off. The product was isolated from the filtrate by lyophilization. Reversed phase HPLC (Nucleosil 300 Å 5 µm C8 column, 250×4 mm id, 0.6 mL/min, solvent A was 1 g TFA in 1 liter water, solvent B was 1 g TFA dissolved in 100 ml water then taken to 1 liter with acetonitrile, gradient from 100% A to 100% B) showed only one major component, which was identified as the expected H-Tyr-('PEG'-succ)$_3$-Leu-OH by electrospray ionization mass spectrometry (found mass 1201.5, calculated 1201.6).

EXAMPLE 3

Synthesis of H-Ser-('PEG'-succ)$_8$-Abu-OH

Eight cycles of PEG-succ were performed on an Abu-Sasrin resin, in a manner similar to that described in Example 1 to yield:

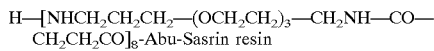
H—[NHCH$_2$CH$_2$CH$_2$—(OCH$_2$CH$_2$)$_3$—CH$_2$NH—CO—CH$_2$CH$_2$CO]$_8$-Abu-Sasrin resin The resin-bound amino group of the 8th 'PEG' was acylated with Fmoc-Ser(t-Bu). A portion of resin was Fmoc deprotected with piperidine and then treated with TFA to remove the butyl side chain protection and cleave from the resin. Another portion was cleaved from the resin using 1% TFA in DCM as recommended by the manufacturer (Bachem), leaving Fmoc and butyl protection intact. It is known (see the brochure on Sasrin resin distributed by Bachem) that Sasrin resin is susceptible to slow (24 hours) aminolysis by diamines, resulting in release of the growing chain as an amide and liberation of a hydroxyl group on the resin. While such a reaction might occur to a small extent during the aminolysis described, any released chain is washed away during subsequent steps and so does not contaminate the product.

Both products gave exceedingly clean chromotograms and the expected masses by mass spectrometry: Fmoc-Ser (But)-('PEG'-succ)$_8$-Abu-OH gave signals at m/z 722.9 and 963.5 corresponding to M+4H+ and M+3H+ respectively, leading to a mass of 2887.5, calculated 2887.5; H-Ser-('PEG'-succ)$_8$-Abu-OH gave signals at m/z 523.0, 653.6 and 871.0 corresponding to M+5H+, M+4H+ and M+3H+ respectively, leading to a mass of 2609.3, calculated 2609.2. No trace of material lacking a —CH$_2$CH$_2$O— (44 amu) was visible in the mass spectrum, which was of sufficient intensity to show impurities down to the 1% level.

The fully protected product was perfectly soluble in the water/acetonitrile/TFA HPLC solvent system. This is an expected property of polyethylene glycols, but fully protected peptides are typically insoluble in most solvents. As is well known, fully protected products with a terminal free carboxylic acid are useful for activation and coupling in segment condensations (convergent syntheses). Upon deprotection of the Ser group, it may be oxidized under very mild conditions with periodate to give an aldehyde group suitable for forming non-peptide bonds (e.g. oximes). Such oxidation and oximation is described in Rose, *J. Am. Chem. Soc.*, supra.

EXAMPLE 4

Synthesis of (H-Ser-('PEG'-succ)$_4$)$_4$Lys$_2$Lys-NHCH$_2$CH$_2$SH

Fmoc-cysteamine Sasrin resin (Bachem, 200 mg, 0.51 mmol/g) was Fmoc-deprotected (less resin was taken than usual as the number of amino groups was to be multiplied as described). Two cycles of Fmoc-Lys(Fmoc) were coupled to create a Lysine "tree" with four free amino groups in place of each original one.

Four cycles of 'PEG'-succ were performed on the resin as described in Example 1. The resin was then acylated with Fmoc-Ser(t-Bu), Fmoc-deprotected, then treated with TFA in the presence of triisopropylsilane to remove butyl and cleave from the resin. The expected product, (H-Ser-('PEG'-succ)$_4$)$_4$Lys$_2$Lys-NHCH$_2$CH$_2$SH, was isolated by HPLC and identified by mass spectrometry (mass 5647.9). The thiol was alkylated in phosphate buffer pH 7 with 5-iodoacetaminofluorescein (Fluka) to yield the expected alkylated four-branched product carrying the fluorophore. The product was isolated by HPLC and characterized by mass spectrometry. It gave signals at m/z 671.9, 755.7, 863.5, 1007.1 and 1208.2 corresponding to M+9H+, M+8H+, M+7H+, M+6H+ and M+5H+ respectively, giving a mass of 6037.0, calculated 6037.2. The Ser residues may be oxidized by mild periodate treatment (which does not affect the fluorophore) and a tetraoxime formed with peptides or other molecules carrying aminooxy groups, as described in Rose, *J. Am. Chem. Soc.*, supra.

The yield of branched product (H-Ser-('PEG'-succ)$_4$)$_4$Lys$_2$Lys-NHCH$_2$CH$_2$SH was much lower than the yields obtained with linear 'PEG'-succ oligomers, even those possessing 8 repeat units, probably due to enhanced propensity for bridging of closely spaced activated carboxyl groups by diamine in the case of the branched structure. For this reason, it may be preferable, when constructing branched structures by oximation, to condense for example the linear 'PEG'-succ-containing compound (peptide)-('PEG'-succ)$_n$-'PEG'-COCH$_2$ONH$_2$ with the branched (O=CHCO—)$_4$Lys$_2$-Lys-NH$_2$ rather than (peptide)-COCH$_2$ONH$_2$ and the branched 'PEG'-succ-containing compound (O=CHCO-('PEG'-succ)$_4$)$_4$Lys$_2$Lys-NH$_2$.

EXAMPLE 5

Synthesis of Peptide Dimers: (Peptide)-oxime-('PEG'-succ)$_{16}$-'PEG'-oxime-(peptide)

Unmodified Sasrin resin (0.25 mmole, Bachem), was used in this example. The resin-bound hydroxyl groups were acylated with SA (10 moles) in 5 ml DMF containing 1 mmole of DMAP for 40 min. This acylation reaction was repeated to ensure a high degree of acylation of the hydroxyl groups of the Sasrin resin. The product at this stage is HOOC—CH$_2$CH$_2$—CO—O—CH$_2$(C$_6$H$_3$(OCH$_3$))—O—CH$_2$-Polystyrene, which is a form of HOOC—X—CO—O—Q-support as described in Scheme 1, where Q is the Sasrin linker —CH$_2$(C$_6$H$_3$(OCH$_3$))—O—CH$_2$—, the support is the polystyrene of the Sasrin beads, and X is —CH$_2$CH$_2$—.

After washing with DMF, the free carboxyl group of the acid was activated with 8 mmole of CDI in 8 ml DMF for 30 minutes.

The activated resin was aminolysed with 'PEG' as described in Example 1. Seven further cycles of 'PEG'-succ were added as in Example 1. (In another case, five further cycles were used instead of seven).

The terminal amino group was then acylated with Boc-Ser(Bzl) using HBTU/DIEA under standard conditions. The chain was removed from the resin by multiple treatments with 1% TFA in DCM, neutralizing each aliquot with pyridine in methanol as recommended by the Sasrin manufacturer. The product at this stage, Boc-Ser(Bzl)-('PEG'-succ)$_7$-'PEG'-COCH$_2$—CH$_2$CO—OH, or more simply Boc-Ser(Bzl)-('PEG'-succ)$_8$—OH, was isolated by rotary evaporation at room temperature and purified by reversed phase HPLC. (In the other case, Boc-Ser(Bzl)-('PEG'-succ)$_6$—OH was made). The carboxyl group was activated for 10 min under standard conditions with HATU (one equivalent) in NMP and the activated compound aminolysed for two days with 'PEG' (half an equivalent, to favor acylation of both amino groups of the 'PEG'). The product was isolated by reversed phase HPLC and characterized by electrospray ionization mass spectrometry as the symmetrical compound:

which can also be written:

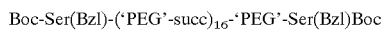

In the above structure, it is to be understood that both terminal amino groups of the symmetrical central 'PEG' have been acylated with Boc-Ser(Bzl)-('PEG'-succ)$_8$-: the right hand Ser(Bzl) is thus —CO—CH(CH$_2$OBzl)NH— rather than the more conventional thus —NH—CH(CH$_2$OBzl)CO— so the Ser residue is shown in italics to indicate this. The mass found was 5613 found (5612.9 calculated). In the other case the product was the symmetrical compound:

which can also be written as:

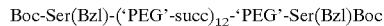

and the mass found was 4403.4 (4403.4 calculated).

Protecting groups (Boc, Bzl) were removed in the standard way by treatment with TFA (20 μl TFA per mg) for 4 min, followed by addition of trifluoromethane sulfonic acid (2 μl per mg) for 25 min at room temperature. The deprotected material was precipitated and washed three times with diethyl ether previously cooled to −20° C. to yield the symmetrical compound:

or

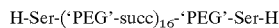

which was isolated by reversed phase HPLC and characterized by electrospray ionization mass spectrometry: mass found 5232, calculated 5232.4.

The unprotected serine groups may be oxidized with HIO$_4$ as described by Rose, J. Am. Chem. Soc., supra) to give terminal aldehyde groups:

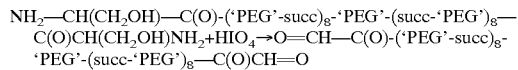

The addition of NH$_2$OCH$_2$C(O)-peptide under standard oximation conditions yields the dumbbell dioxime:

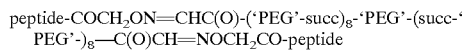

which may also be written:

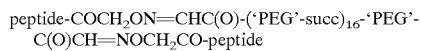

or

which may be isolated by HPLC and characterized by mass spectrometry.

An example of a suitable peptide sequence to use is the one described by Johnson, et al., Chemistry & Biology, supra: -Gly-Gly-Leu-Tyr-Ala-Cys-His-Met-Gly-Pro-Met-Thr-Trp-Val-Cys-Gln-Pro-Leu-Arg-Gly-(SEQ ID NO:1).

Dimerization of this peptide with linker of molecular weight about 3400 was shown to lead to an increase of about 1000-fold in biological activity. Example 7 describes how this peptide was produced in appropriate form (aminooxyacetyl group and disulfide bond present) for oximation to the oxidized PEG-linker.

EXAMPLE 6

Synthesis of Peptides Attached to PEG-linkers: (Peptide)-Lys(NH$_2$OCH$_2$CO-('PEG'-succ)$_8$-)-amide MBHA resin (0.5 mmole, Novabiochem, Switzerland), was used in this example. The resin-bound amino groups were acylated with Fmoc-Lys(Mtt) under standard conditions. After removal of the Fmoc group (20% piperidine in DMF, 20 min), eight cycles of 'PEG'-succ were added under the conditions of Example 1. The terminal amino group of the eighth 'PEG' group was acylated with Boc-Glu(Ochxl).

The Mtt group (but not the Boc group) was then removed with aliquots of 1% TFA in DCM until no more yellow color was released. The free amino group was acylated with Fmoc-O-Su (1 mmole in 4 ml DMSO containing 0.4 ml N-methylmorpholine, 1 hour; check with Kaiser test and repeat acylation if necessary but the second time using only 0.2 ml N-methylmorpholine) prior to extension of the peptide chain using standard Boc chemistry with the sequence:

H-Ser-Val-Trp-Arg-Trp-Leu-Pro-Tyr-Asp-Lys-Tyr-(SEQ ID NO:2)

The sequence H-Ser-Val-Trp-Arg-Trp-Leu-Pro-Tyr-Asp-Lys-Tyr-Glu-(SEQ ID NO:3) has been described in Terskikh, et al., supra. Five copies of this peptide, when properly spaced, gave five orders of magnitude better binding to a pathological cell line.

The Fmoc group (and the formyl group on the side chain of tryptophan) was removed with piperidine in DMF and the free amino group was acylated with Boc-NHOCH$_2$CO-OSu (exactly as the Fmoc-O-Su coupling just described). The Boc group was removed with TFA, the resin was neutralized with 10% DIEA in DMF, washed with DMF followed by DCM:MeOH 1:1 and dried under high vacuum. Cleavage with HF and product isolation was performed as in Example 2. The product, isolated by reversed phase HPLC, was characterized by electrospray ionization mass spectrometry: H-Ser-Val-Trp-Arg-Trp-Leu-Pro-Tyr-Asp-Lys-Tyr-Glu-Lys(NH$_2$OCH$_2$CO-('PEG'-succ)$_8$)-NH$_2$ (SEQ ID NO:4), found mass 4261.9, calculated 4261.1.

A compound with a shorter linker was prepared as above but using only 4 cycles of 'PEG'-succ. This compound gave a mass of 3051.5 found, 3051.6 calculated.

These peptides with PEG-based linkers and aminooxyacetyl groups (NH$_2$OCH$_2$CO—) are used in oximation reactions to make dimers and higher order polyoximes using chemistry described in Rose, *J. Am. Chem. Soc.*, supra.

EXAMPLE 7

Synthesis of Peptide Dimers: (Peptide)-oxime-('PEG'-succ)$_2$-Lys((peptide)-oxime-('PEG'-succ)$_2$) amide MBHA resin (0.5 mmole, Novabiochem, Switzerland), was used in this example. The sequence: Gly-Gly-Leu-Tyr-Ala-Cys-His-Met-Gly-Pro-Met-Thr-Trp-Val-Cys-Gln-Pro-Leu-Arg-Gly-(SEQ ID NO:1) (described by Johnson, et al., *Chemistry & Biology*, supra)), followed by Boc-aminoacetic acid was coupled to the resin by standard Boc chemistry on the ABI 430A machine. The dinitrophenyl group was removed from the side-chain of His by two 30 minute treatments with 10 ml volumes of a mixture of mercaptoethanol (6 ml) and DIEA (3 ml) in DMF (21 ml). After washing the resin with DMF, the Boc group was removed with TFA in the standard way, then the formyl group was removed from tryptophan by two treatments with 10 ml portions of a mixture of water (2 ml) and ethanolamine (2.4 ml) in DMF (35.6 ml). The resin was washed thoroughly with DMF followed by DCM then DCM/methanol (1:1), drained and then dried under high vacuum. Cleavage and deprotection with hydrogen fluoride, and product isolation was as described in Example 2. Electrospray ionization mass spectrometry showed the product to have the expected mass (2250.8 found, 2249.7 calc.) for: NH$_2$OCH$_2$CO-Gly-Gly-Leu-Tyr-Ala-Cys-His-Met-Gly-Pro-Met-Thr-Trp-Val-Cys-Gln-Pro-Leu-Arg-Gly-NH$_2$(SEQ ID NO:1).

The disulfide bond was formed as follows. 48 mg of the above peptide (about 21.3 micromoles) was dissolved in 48 ml water and the pH adjusted to 7.0 (glass electrode) with ammonium hydroxide solution. 25 equivalents of a stock solution of 0.92 M hydrogen peroxide was added. After 30 min at room temperature, the solution was acidified with 0.5 ml acetic acid and immediately injected onto preparative reversed phase HPLC. Formation of the disulfide bond was confirmed by the loss of two mass units: found 2247.8, calculated 2247.7.

MBHA resin (0.5 mmole, Novabiochem, Switzerland), was used in this example. The resin-bound amino groups were acylated with Fmoc-Lys(Fmoc) under standard conditions. After removal of the Fmoc groups (20% piperidine in DMF, 20 min), two cycles of 'PEG'-succ were added under the conditions of Example 1. The terminal amino groups of the 'PEG' groups were then acylated with Boc-Ser(Bzl). After removal of the Boc groups with TFA and washing and drying of the resin, the resin was treated with liquid hydrogen fluoride and the product isolated as in Example 2. Reversed phase HPLC showed a single major product, which was characterized as the expected product by electrospray ionization mass spectrometry (found 1529.4, calculated 1528.8): H-Ser-'PEG'-succ-'PEG'-succ-Lys(H-Ser-'PEG'-succ-'PEG'-succ)NH$_2$ The yield was 180 mg purified product. The terminal serine residues were oxidized with periodate in mixture of imidazole buffer (340 mg imidazole in 100 ml water, adjusted to pH 6.95 with 6 M HCl) and acetonitrile, 7:2 by volume under conditions described by Gaertner, et al., *Bioconjugate Chemistry* 3:262–268 (1992). After isolation of the oxidized (dialdehyde) product by reversed phase HPLC, it was characterized by mass spectrometry: masses found 1466.9, 1484.9 and 1502.9, corresponding to the expected dialdehyde, to the monohydrate and the dihydrate, respectively (calculated 1466.8, 1484.8, 1502.8, respectively):

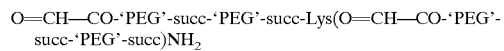

O=CH—CO-'PEG'-succ-'PEG'-succ-Lys(O=CH—CO-'PEG'-succ-'PEG'-succ)NH$_2$

After preparative HPLC in 0.1% TFA with a gradient of 0.1% TFA in 90% acetonitrile, the dialdehyde is recovered by rotary evaporation at room temperature to a concentration of about 10 mM (the oxidation is quantitative).

Oximation (according to Rose, K., 1994) of the dialdehyde with a two-fold excess of: NH$_2$OCH$_2$CO-Gly-Gly-Leu-Tyr-Ala-Cys-His-Met-Gly-Pro-Met-Thr-Trp-Val-Cys-Gln-Pro-Leu-Arg-Gly-NH$_2$ (SEQ ID NO:1) (having a disulfide bond) for 18 hours at room temperature led to formation of the expected dioxime between this peptide and the dialdehyde. The dioxime was isolated by reversed phase HPLC and characterized by mass spectrometry: mass found 5926.0, calculated 5926.0.

EXAMPLE 8

Synthesis of H-('PEG'-succ)$_7$-'PEG'-H

After swelling in DMF, Sasrin resin (0.3 mmole) was activated with CDI (8 mmole in 8 ml NMP, which was 0.5 M in 4-dimethylaminopyridine) for 30 minutes, drained, and the activation repeated once. This activated resin was aminolysed with 'PEG', then acylated with SA and used to prepare H-('PEG'-succ)$_7$-'PEG'-CO—O—CH$_2$—C$_6$H$_3$(OCH$_3$)-resin as previously described, except that NMP was used in place of DMF except for washing steps. Product was cleaved from the resin with TFA for 30 minutes and precipitated with cold diethylether (at its freezing point). The product was isolated by preparative reversed phase HPLC. Electrospray mass spectrometry showed a mass of 2437.18±0.81. Calculated mass for the symmetrical H-('PEG'-succ)$_7$-'PEG'-H was 2436.98.

EXAMPLE 9

Synthesis of H-('DAH'-succ-'PEG'-succ)$_3$-'DAH'-succ-'PEG'-H

This example follows a similar procedures as that set forth in Example 8, except that 'DAH' was used in place of 'PEG' in alternate aminolysis cycles. In this way, ('DAH'-succ-'PEG'-succ)$_3$-'DAH'-succ-'PEG' was made on Sasrin resin. The use of NMP in place of DMF in the methods of Examples 1 and 5–7 is advantageous when working with a hydrophobic diamine such as DAH, although DMF is preferred when working with the more hydrophilic 'PEG' diamine. After cleavage from the resin with TFA and precipitation with cold diethylether (at its freezing point), the product was isolated by reversed phase HPLC. Electrospray mass spectrometry showed a mass of 1920.78±0.59. Calculated mass for H-('DAH'-succ-'PEG'-succ)$_3$-'DAH'-succ-'PEG'-H was 1920.49.

EXAMPLE 10

Evaluation of Polyamide Stability

The compounds produced in Examples 8 and 9 were separately dissolved at 1 mg/ml in a 1% ammonium bicarbonate solution. In separate tubes, these solutions were treated with trypsin, chymotrypsin and elastase (enzyme:substrate ratio 1:100, 37° C.). Aliquots (20 µl) were withdrawn at intervals and analyzed by HPLC. No digestion occurred even after 24 hours, whereas control incubations of insulin with the enzymes under the same conditions showed extensive digestion after a mere 4 hours. The polyamides are thus much more stable than polypeptides to attack by proteases. In contrast, the peptide amide H-Pro-Gln-Pro-Gln-Pro-Lys-Pro-Gin-Pro-Gln-Pro-Gln-Pro-Gln-Pro-Lys-Pro-Gln-Pro-Lys-Pro-Glu-Pro-Glu-NH$_2$ (SEQ ID NO:5) from the hinge region of camel antibodies used by Terskikh et al., supra, while it was stable to chymotrypsin and elastase, it was digested extensively by trypsin over 24 hours.

EXAMPLE 11

A. Synthesis of an EMP-dimer (Commercial PEG) and HPLC/Mass Spectrometry Analysis An EMP-dimer, referred to herein as the "commercial EMP-dimer", was made using the commercial PEG dialdehyde linker of mean relative molecular mass 3400 (Shearwater Polymers), referred to herein as the "commercial EMP-dimer" and denoted O=CH-commercial PEG-CH=O. The monomeric peptide (Johnson, et al., *Chemistry & Biology*, supra) carrying an AoA group, NH$_2$OCH$_2$CO-GGLYACHMGPMTWVCQPLRG-amide (SEQ ID NO:1) and a disulfide bond was synthesized using standard techniques by Boc chemistry on MBHA resin (Fields, supra and Rose, *J. Am. Chem. Soc.*, supra and example 7). The peptide was then cleaved from the resin and deprotected with HF (containing 5% p-cresol, 0° C. for 60 min), precipitated with diethylether and purified by preparative HPLC. Oximation was then performed with the commercial PEG linker to give the dimer: amide-GRLPQCVWTMPGMHCAYLGG-COCH$_2$ON=CH-commercial PEG-CH=NOCH$_2$CO-GGLYACHMGPMTWVCQPLRG-amide (a dimer of SEQ ID NO:1). Italics are used to indicate that one of the peptides is depicted in the unconventional orientation (C to N terminus rather than the conventional N to C terminus). Oximation was done as follows: 2.4 mg EMP peptide (1.06 µmol; 1.2-fold excess over aldehyde groups) was dissolved in 0.2 ml water and added to 1.5 mg (0.44 µmoles) PEG-dialdehyde dissolved in 0.45 ml acetate buffer (0.15 M, counterion sodium, 6M in guanidine hydrochloride). After 16 hours in the dark at room temperature, the product was isolated by preparative HPLC and characterized by analytical HPLC and MALDI-TOF mass spectrometry.

The reverse phase HPLC chromatogram and mass spectrometric analysis of this EMP-dimer utilized the MALDI-TOF technique (which leads to singly protonated species) because the spectrum was too complex for analysis on the electrospray quadruple machine (which leads to multiply protonated species).

Previous work with such dimers (Johnson, et al., *Chemistry & Biology*, supra), made with commercial PEG from the same supplier, demonstrated an ED$_{50}$ of 0.1 nM in an EPO-dependent cell proliferation assay, 1000-fold lower than that of the peptide monomer. In spite of its clean chromatogram, the mass spectrum showed more than 40 components, each differing by the PEG repeat unit, —CH$_2$CH$_2$O—, a spacing of 44 amu. It was not possible to separate the individual components by HPLC. The mass peak at the center of the distribution (8024 amu) corresponded to a molecule with 78 —CH$_2$CH$_2$O— groups, consistent with the declared relative molecular mass of the PEG (3400, i.e. 77 repeat units, 231 bonds, found here to be ±20 repeat units or 60 bonds).

B. Synthesis of an EMP-dimer (Precise Length PEG) and HPLC/Mass Spectrometry Analysis An EMP-dimer, referred to herein as the "precise length EMP-dimer", was made using one of the precise length PEG-based polyamide chains of the invention (referred to herein as the "precise length EMP-dimer"). The precise length EMP-dimer had a length longer than the commercial EMP-dimer.

The precise length EMP-dimer was based upon the symmetrical polyamide linker, -('PEG'-succ)$_6$-'PEG'-(succ-'PEG')$_6$-, and was synthesized as follows.

The PEG-polyamide linker, Boc-Ser(Bzl)-('PEG'-succ)$_6$—OH was prepared on Sasrin resin (Bachem) using the techniques described above. The material was cleaved from the resin with 1% TFA in DCM as recommended by the resin manufacturer and purified by preparative HPLC. To a solution of Boc-Ser(Bzl)-(PEG-succ)$_6$—OH (9.7 mg, 4.4 µmol) in NMP were added HATU reagent (1.6 mg, 4.4 µmmol) and a solution of DIEA diluted 10 fold in NMP (15 µl, 8.8 µmol) with stirring. After 5 min corresponding to the preactivation of the carboxylic acid group, the active ester was aminolysed with the PEG-based diamine (4,7,10-trioxa-1,1 3-tridecanediamine, 'PEG', diluted 100 fold with NMP, 24 µl 1.15 µmol) overnight. The resulting symmetrical Boc-Ser(Bzl)-('PEG'-'succ')$_6$-'PEG'-(succ-'PEG')$_6$-Ser(Bzl)-Boc was directly purified by preparative HPLC (Yield 7 mg, 1.6 µmol, 73%). The two Boc groups and benzyl groups were removed with the standard TFMSA cleavage procedure (300 µl TFA for 4 min followed by addition of 30 µl TFMSA for 25 min). The product was precipitated with cold diethylether (at its melting point, a little solid ether was present), washed three times with cold ether and dried in a desiccator. The Ser residues of the deprotected linker Ser-('PEG'-succ)$_6$-'PEG'-(succ-'PEG')$_6$-Ser were oxidized to glyoxylyl functions (O=CH—CO—), as described in Rose, *J. Am. Chem. Soc.*, supra. The second Ser is shown in italics to indicate the fact that the linker is symmetrical: the first Ser is NH$_2$—CH(CH$_2$OH)CO— and the second Ser is —CO—CH(CH$_2$OH)—NH$_2$ i.e. shown the unconventional way round.

The resulting dialdehyde linker was repurified by HPLC. A solution of the aminooxyacetyl-EMP peptide derivative with its disulfide bond formed, (96 µl, 21.3 mM in 0.1 M acetate buffer, pH 4.0, counterion sodium; a 1.5-fold excess over aldehyde groups) was mixed with the dialdehyde (200 µl, 3.5 mM in water) and left to react at room temperature for 48 hours. The dimeric product: amide-GRLPQCVWTMPGMHCAYLGG-COCH$_2$ON=CH—CO-('PEG'-succ)$_{12}$-'PEG'-CH=NOCH$_2$CO-*GGLYACHMGPMTWVCQPLRG*-amide (a dimer of SEQ ID NO:1) was isolated by reversed phase HPLC, with a yield of 1.2 mg (20%) and characterized by analytical HPLC and electrospray ionization mass spectrometry. Italics are used to indicate that one of the peptides is depicted in the unconventional orientation (C to N terminus rather than the conventional N to C terminus).

Although the precise length EMP-dimer had more bonds than the commercial EMP-dimer (243 versus 231) and 42 —CH$_2$CH$_2$O— units, the precise length EMP-dimer was much more homogeneous. In the mass spectrum there was no sign of material with one too few —CH$_2$CH$_2$O— repeats (44 mass units). The signals which were slightly more massive than the principal signal were due to cationization with sodium and potassium, a common feature of electrospray ionization mass spectra. The mass found (8417) was very close to the theoretical value of 8420.

It proved possible to make dimers with longer and shorter chains: 16 and 4-'PEG'-succ- repeat units. Excellent chromatograms and mass spectra were obtained using spacers up to -('PEG'-succ)$_8$-'PEG'-(succ-'PEG')$_8$-.

EXAMPLE 12

Precise Length EMP-dimers with linkers of different lengths were assayed for EPO activity in a cell culture assay (human leukemic UT-7 EPO dependent cell line). Recombinant EPO and the EMP monomer peptides were included as controls, where the monomer is designated as "mono" in Table 1.

The short linker in the precise length EMP-dimer (designated "s" in Table 1) was -('PEG'-succ)$_2$-'PEG'-(succ-'PEG')$_2$-. The medium linker (designated "m" in Table 1) was -('PEG'-succ)$_6$-'PEG'-(succ-'PEG')$_6$- and the long linker (designated "l" in Table 1) was -('PEG'-succ)$_8$-'PEG'-(succ-'PEG')$_8$-.

Table 1 presents the mean OD's for each peptide sample.

TABLE 1

| Concentration (µM) | OD m | OD s | OD l | OD mono |
|---|---|---|---|---|
| 1 × 10$^{-1}$ | .884 | .930 | .891 | .878 |
| 3.33 × 10$^{-2}$ | .902 | .925 | .890 | .673 |
| 1.11 × 10$^{-2}$ | .876 | .935 | .906 | .373 |
| 3.70 × 10$^{-3}$ | .888 | .919 | .931 | .210 |
| 1.24 × 10$^{-3}$ | .916 | .798 | .838 | .078 |
| 4.12 × 10$^{-4}$ | .805 | .756 | .848 | .078 |
| 1.37 × 10$^{-4}$ | .760 | .534 | .835 | .089 |
| 4.57 × 10$^{-5}$ | .637 | .299 | .695 | " |
| 1.52 × 10$^{-5}$ | .597 | .194 | .632 | " |
| 5.08 × 10$^{-6}$ | .712 | .171 | .525 | " |
| 1.69 × 10$^{-6}$ | .641 | .298 | .614 | " |
| 5.65 × 10$^{-7}$ | .469 | .163 | .547 | " |
| 1.88 × 10$^{-7}$ | .363 | .117 | .502 | " |
| 6.27 × 10$^{-8}$ | .350 | .114 | .356 | " |
| 2.09 × 10$^{-8}$ | .287 | .088 | .231 | " |
| 6.97 × 10$^{-9}$ | .280 | .089 | .193 | " |
| 2.32 × 10$^{-9}$ | .246 | .083 | .217 | " |
| 7.74 × 10$^{-10}$ | — | .099 | .194 | " |

TABLE 1-continued

| Concentration (µM) | OD m | OD s | OD l | OD mono |
|---|---|---|---|---|
| 2.58 × 10$^{-10}$ | — | .129 | .170 | " |
| neg control | .089 | .076 | .074 | .090 |

Table 2 presents the mean OD's for recombinant EPO sample.

TABLE 2

| EPO (ng/ml) | OD |
|---|---|
| 50 | .917 |
| 16.7 | .920 |
| 5.56 | .885 |
| 1.85 | .878 |
| .617 | .650 |
| .206 | .362 |
| .0686 | .179 |
| .0229 | .124 |
| .00762 | .108 |
| .00254 | .101 |
| neg control | .078 |

It was clear, from the results presented above, that the ED$_{50}$ (effective dose giving 50% of maximum response) values were as presented in Table 3.

TABLE 3

| Material | ED$_{50}$ (pM) |
|---|---|
| EMP monomer | 20,000 |
| Recombinant EPO | 25 |
| EMP-s (short dimer) | 100 |
| EMP-m (medium dimer) | 1 |
| EMP-l (long dimer) | 0.1 |

Table 3 shows that the EMP dimers linked with medium and long polyamide chains were much more active in the cellular assay than the recombinant protein standard.

EXAMPLE 13

The following experiment explored the use of branched structures with polymers other than PEG used in their construction.

The PEG-based polyamides of the invention were used to synthesize a chemical version of the peptabody (Terskikh, et al., supra) which is referred to herein as a "chemobody". The monomeric peptide carrying an AoA group, H-ADGACRNPWC-('PEG'-succ)$_8$-Lys(AoA)-amide (SEQ ID NO:6), was synthesized on Fmoc-Lys(Mtt)-MBHA resin (0.5 mmol) by standard techniques (Fields, supra and Rose, J. Am. Chem. Soc., supra). Briefly, Fmoc protection was removed, 8 cycles of 'PEG'-succ were performed, then Boc-Cys(4-MeBzl) was coupled to the terminal amino group. Mtt protection was removed (multiple rounds of 1% TFA in DCM until the solution was no longer yellow) and the amino group acylated with Fmoc-OSu (2 mmol in 5 ml DMF with N-methylmorpholine as base). The peptide chain was extended out to the N-terminus by Boc chemistry. Fmoc protection was removed with 10% piperidine in DMF for 7 minutes since stronger conditions led to succinimide formation at Asp-Gly. This piperidine treatment removes formyl protection from the Trp indole. The amino group was acylated with Boc-AoA-OSsu (0.6 mmol in 5 ml dry DMSO with N-methylmorpholine as base, not more forcing conditions or acylation of Trp or of the N of Boc-NHOCH$_2$CO— occurs). After cleavage from the resin and deprotection with HF, purification by HPLC, disulfide bond formation with hydrogen peroxide as described for the EMP peptide, the product was isolated by HPLC and characterized by analytical HPLC and electrospray ionization mass spectrometry: mass found 3709.1, theoretical 3709.4.

A tetravalent template Ser-Lys(Ser)-Lys(Ser-Lys(Ser))-NHCH$_2$—CH$_2$SH was prepared by standard techniques starting with Fmoc-cysteamine-Sasrin resin (Bachem) and coupling two rounds of Fmoc-Lys(Fmoc) then Boc-Ser(t-Bu). After deprotection and cleavage (270 mg resin, 2.7 ml TFA, 30 min, filtered, evaporated under a nitrogen stream to small volume, precipitated with cold diethylether), the product was purified by HPLC. The thiol group was alkylated as follows: to a solution of phosphate buffer (2.5 ml, 0.25 M phosphate pH 7.0, 1 mM in EDTA) was mixed in first 1 ml purified template (10 mM in water) and immediately afterwards 5-iodoacetaminofluorescein (Fluka, 1 ml, 10 mM in DMF) was mixed in. After 90 min in the dark, the fluorescein-labeled template was purified by HPLC: yield 7.8 mg, 66%. After oxidation of the Ser residues and isolation by HPLC, the tetra-glyoxylyl fluorescein-labeled template (28 µl, 3.4 mM in water) was oximated with H-ADGACRNPWC-('PEG'-succ)$_8$-Lys(AoA)-amide (SEQ ID NO:6) (disulfide form, 66 µl, 6 mM in 0.1 M acetate buffer, pH 4.0, counter-ion sodium, 1.04-fold excess over each aldehyde group present) at room temperature for 48 hours. The product was purified by HPLC and characterized analytical HPLC and electrospray ionization mass spectrometry: [peptide-('PEG'-succ)$_8$-Lys(oxime)amide]$_4$Lys$_2$Lys-NHCH$_2$CH$_2$S—CH$_2$C(O)NH-fluorescein, where the "peptide" is -ADGACRNPWC-(SEQ ID NO:6).

By analogy with the peptabody of Terskikh et al., supra, this tetrameric product is referred to as a tetrameric chemobody. HPLC chromatogram and mass spectrum of this tetrameric chemobody displayed four copies of the phage-derived peptide ADGACRNPWC-(SEQ ID NO:6) (with a disulfide bond between the cysteines) which bound to the BCL, turnor cell line (Terskikh, et al., supra). In comparison with the Terskikh peptabody, which has five peptides, a linker length of 72 bonds and no reporter group for a relative molecular mass of 85,000, the chemobody has 4 binding peptides, a PEG-polyamide spacer length of 167 bonds and a fluorescein reporter group for a relative molecular mass of 15,858 (found; close to the theoretical 15839). A small signal at mass 15,521 corresponded to a very minor component with a single -'PEG'-succ- repeat unit missing out of the 32 present.

Such deletions are common in solid phase peptide synthesis, and as with standard peptide chemistry, optimization of the coupling steps (higher concentrations, longer times, higher temperatures, better solvents, additives such as 4,4'-dimethylaminopyridine) would be expected to yield even longer chains especially as, with these unhindered and very soluble compounds, there should be none of the difficult sequences found with peptides and generally associated with beta-structure formation.

Phage-derived peptides may thus be displayed on a totally synthetic molecule on the tips of biocompatible chains without the problems associated with recombinant expression and refolding. By the method described above, chemobodies were easily made with ADGACRNPWC (SEQ ID NO:6), as well as with the phage peptide SVWRWLPYDKYE, (SEQ ID NO:3) whereas the corresponding peptabodies with the corresponding sequence could not be produced in soluble form (Terskikh, et al., supra). A wide range of precisely made dimers and multivalent structures such as the chemobody can now be readily synthesized by the methods described herein.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A branched water-soluble polyamide composition comprising two or more water-soluble organic polyamide-based chains having a precise number of repeating units, said polyamide-based chains covalently attached through a multivalent linker to a moiety selected from the group consisting of a target molecule, a terminal group, a protecting group, and a reactive group, said water-soluble organic polyamide-based chains having a repeat unit of the formula:

$$-\{NH-Y-NH-CO-X-CO\}_n-$$

wherein X and Y are divalent organic radicals lacking reactive functional groups or are absent, and can be the same or different, and can vary independently with each of said repeating units; n is an integer from 2 to 100; and wherein said water-soluble organic polyamide-based chains contain a sufficient number of water-soluble repeat units to render said composition water-soluble.

2. The branched water-soluble polyamide composition of claim 1, wherein said multivalent linker comprises one or more divalent linkers or spacers.

3. The branched water-soluble polyamide composition of claim 2, wherein one or more of said water-soluble polyamide chains is covalently attached to said multivalent linker through said divalent linker or spacer.

4. The branched water-soluble polyamide composition of claim 2, wherein one or more of said target molecule, terminal group, protecting group, and reactive group are covalently attached to said multivalent linker through said divalent linker or spacer.

5. The branched water-soluble polyamide composition of claim 1, wherein said water-soluble polyamide chains have a terminal end group comprising a moiety selected from the group consisting of a target-molecule, a terminal group, a protecting group, and a reactive group.

6. The branched water-soluble polyamide composition of claim 5, wherein said terminal end group comprises a divalent linker or spacer and one or more of said target molecule, terminal group, protecting group, and reactive group are covalently attached to one or more of said water-soluble polyamide chains through said divalent linker or spacer.

7. The branched water-soluble polyamide composition of claim 1, wherein n is an integer from 2 to 50.

8. The branched water-soluble polyamide composition of claim 1, wherein n is an integer from 3 to 32.

9. The branched water-soluble polyamide composition of claim 1, wherein n is an integer from 4 to 16.

10. The branched water-soluble polyamide composition of claim 1, wherein n is an integer from 6 to 12.

11. The branched water-soluble polyamide composition of claim 1, wherein said water-soluble organic polyamide-based chains are homogenous.

12. The branched water-soluble polyamide composition of claim 1, wherein said composition is homogenous.

13. The branched water-soluble polyamide composition of claim 1, wherein said multivalent linker comprises one or more lysine residues.

14. The branched water-soluble polyamide composition of claim 1, wherein said multivalent linker comprises a lysine tree.

15. The branched water-soluble polyamide composition of claim 14, wherein said lysine tree comprises a radical of the formula -Lys$_2$-Lys-, where Lys is lysine.

16. The branched water-soluble polyamide composition of claim 1, wherein one or more of said divalent radicals are symmetrical radicals.

17. The branched water-soluble polyamide composition of claim 1, wherein said divalent radicals are symmetrical radicals.

18. The branched water-soluble polyamide composition of claim 1, wherein said divalent organic radicals are selected from the group consisting of substituted, unsubstituted, branched and linear, aliphatic and aromatic groups, and may optionally contain heteroatoms.

19. The branched water-soluble polyamide composition of claim 1, wherein said divalent organic radicals are selected from the group consisting of phenyl, a heteroatom-containing phenyl, a C1–C10 alkyl group, a heteroatom-containing C1–C10 alkyl group, and a combination thereof.

20. The branched water-soluble polyamide composition of claim 1, wherein said divalent organic radicals are selected from the group consisting of —(CH$_2$)$_2$—, —(CH$_2$)$_6$—, —(CH$_2$)$_3$—(OCH$_2$CH$_2$)$_3$—CH$_2$—, —(CH$_2$)$_3$—O—(CH$_2$)$_2$—(CH$_2$)$_2$—O—(CH$_2$)$_3$—, —CH$_2$—O—CH$_2$— and —CH$_2$—N(CH$_3$)—CH$_2$—.

21. The branched water-soluble polyamide composition of claim 1, wherein said repeating units are polyethylene glycol-based monomer units.

22. The branched water-soluble polyamide composition of claim 21, wherein said polyethylene glycol-based monomer units comprise a divalent organic radical of the formula —a—(OCH$_2$CH$_2$)$_p$—b—, where a and b are divalent organic radicals lacking reactive functional groups that may be the same or different, and present or absent, and where p is an integer that is small enough for the monomer unit to have a discrete value of p rather than a range.

23. The branched water-soluble polyamide composition of claim 1, wherein said target molecule is a monovalent or multivalent target molecule whose properties or being modified or enhanced.

24. The branched water-soluble polyamide composition of claim 1, wherein said target molecule comprises a modified target molecule selected from the group consisting of a solid support, amino acid, reporter group, peptide, polypeptide, protein, nucleic acid, therapeutic agent and liposome.

25. The branched water-soluble polyamide composition of claim 1, wherein said protecting group is selected from the group consisting of Boc-, Fmoc-, butyl-, and benzyl-based protecting groups.

26. The branched water-soluble polyamide composition of claim 1, wherein said reactive group is a reactive functional group.

27. The branched water-soluble polyamide composition of claim 26, wherein said reactive functional group is selected from the group consisting of amino, carboxyl, thiol, alkyl halide, hydroxy and aldehyde.

28. The branched water-soluble polyamide composition of claim 1, wherein said reactive group is suitable for the cross-linking of polymers or the conjugation of biomolecules.

29. The branched water-soluble polyamide composition of claim 28, wherein said reactive group suitable for the cross-linking of polymers or the conjugation of biomolecules is selected from the group consisting of alkyl thiol, bromoacetyl, aminoacyl, aminooxyacetyl, glyoxylyl, mercaptoacetyl, and mercaptopropionyl.

30. The branched water-soluble polyamide composition of claim 1, wherein said reactive group comprises a reactive group of an amino acid.

31. The branched water-soluble polyamide composition of claim 1, wherein said terminal group comprises a multivalent linker.

32. The branched water-soluble polyamide composition of claim 1, wherein said terminal group is selected from the group consisting of —OH, —NH$_2$, —H, and —Z—Q—support, where Z is a divalent linker or spacer or may be absent, Q is a linker or a target molecule, and the support is a solid phase, matrix or surface.

33. The branched water-soluble polyamide composition of claim 1, wherein said terminal group comprises a reactive group.

34. The branched water-soluble polyamide composition of claim 33, wherein said reactive group is protected.

35. The branched water-soluble polyamide composition of claim 33, wherein said reactive group is selected from the group consisting of glyoxyl, aldehyde, aminooxyacetyl, amino, hydroxyl, thiol, and an aliphatic acyl group.

36. The branched water-soluble polyamide composition of claim 33, wherein said terminal group comprises an amino acid.

37. The branched water-soluble polyamide composition of claim 36, wherein said amino acid is orthogonally protected.

38. The branched water-soluble polyamide composition of claim 1, wherein said composition comprises the formula:

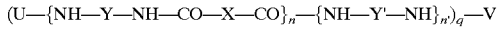

(U—{NH—Y—NH—CO—X—CO}$_n$—{NH—Y'—NH}$_{n'}$)$_q$—V wherein Y' is a divalent organic radical lacking reactive functional groups or is absent and is the same or different compared to substituents X and Y, and can vary independently with each of said chains; n' is 0 or 1; q is an integer from 2 to 10; U and V are selected from the group consisting of a target molecule, a terminal group, a protecting group, and a reactive group, and wherein V comprises said multivalent linker.

39. The branched water-soluble polyamide composition of claim 38, wherein U comprises a divalent linker or spacer that covalently attaches said polyamide-based chain to one or more of said target molecule, terminal group, protecting group and reactive group.

40. The branched water-soluble polyamide composition of claim 39, wherein said divalent linker or spacer comprises a water-soluble organic polyamide-based chain having a precise number of repeating units.

41. The branched water-soluble polyamide composition of claim 39, wherein is selected from the group consisting of: a monovalent or multivalent target molecule having an optional divalent spacer or linker; a peptide chain; a reporter group having a multivalent linker; a reactive group; and a terminal group having a multivalent linker, said terminal group being selected from the group consisting of —OH, —NH$_2$, —H, and —Z—Q-support, where Z is a divalent linker or spacer or may be absent, Q is a linker or a target molecule, and the support is a solid phase, matrix or surface.

42. The branched water-soluble polyamide composition of claim 41, wherein Z is selected from the group consisting of —NH— and —O—.

43. The branched water-soluble polyamide composition of claim 38, wherein U is selected from the group consisting of: a target molecule whose properties are being modified or enhanced and having an optional divalent spacer or linker; a terminal group; a peptide chain, a protecting group; a support; and a reactive group.

44. The branched water-soluble polyamide composition according to any one of claims 41, or 43, wherein said optional divalent linker is an oxime linker.

45. The branched water-soluble polyamide composition according to any one of claims 41, or 43, wherein said optional divalent linker is an oxime linker having the formula —COCH$_2$ON=CH—CO—.

46. The branched water-soluble polyamide composition of claim 41, wherein Q is a linker containing a cleavable moiety or a target molecule bound to the support by a linker containing a cleavable moiety.

47. The branched water-soluble polyamide composition of claim 41, wherein Q is a linker selected from the group consisting of —CH$_2$(C$_6$H$_3$(OCH$_3$))—O—CH$_2$—, —C(O)O—CH$_2$(C$_6$H$_3$(OCH$_3$))—O—CH$_2$—, an aminooxyacetyl, —CO—CH$_2$ON=CH—CO—, and —CH=NOCH$_2$—CO—.

48. The branched water-soluble polyamide composition of claim 38, having the formula:

(U—{NH—CH$_2$—(CH$_2$CH$_2$O)$_3$—(CH$_2$)$_3$—NH—CO—(CH$_2$)$_2$—CO}$_n$)$_q$—V wherein n is an integer from 1–50.

49. The branched water-soluble polyamide composition of claim 38, having the formula:

(U—{NH—(CH$_2$)$_6$—NH—CO—(CH$_2$)$_2$—CO—NH—(CH$_2$)$_3$—(OCH$_2$CH$_2$)$_3$—CH$_2$—NH—CO—(CH$_2$)$_2$—CO}$_n$)$_q$—V wherein n is an integer from 1–50.

50. The branched water-soluble polyamide composition of claim 38, wherein said target molecule is a peptide of less than 50 amino acid residues and having an optional divalent spacer or linker.

51. The branched water-soluble polyamide composition of claim 50, wherein said peptide is selected from the group consisting of:

-GGLYACHMGPMTWVCQPLRG-(SEQ ID NO:1);
-SVWRWLPYDKYE-(SEQ ID NO:3); and
-ADGACRNPWC-(SEQ ID NO:6).

52. A branched water-soluble polyamide comprising the formula:

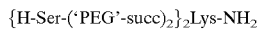
{H-Ser-('PEG'-succ)$_2$}$_2$Lys-NH$_2$ wherein 'PEG' represents the formula —NH—(CH$_2$)$_3$—(OCH$_2$CH$_2$)$_3$—CH$_2$—NH—; and succ represents the formula —CO—(CH$_2$)$_2$—CO—.

53. A branched water-soluble polyamide comprising the formula:

{O=CH—CO—('PEG'-succ)$_2$}$_2$Lys-NH$_2$ wherein 'PEG' represents the formula —NH—(CH$_2$)$_3$—(OCH$_2$CH$_2$)$_3$—CH$_2$—NH—; and succ represents the formula —CO—(CH$_2$)$_2$—CO—.

54. A branched water-soluble polyamide comprising the formula:

{peptide(oxime)-('PEG'-succ)$_2$}$_2$Lys-NH$_2$ wherein said peptide comprises the sequence -GGLYACHMGPMTWVCQPLRG-(SEQ ID NO:1); oxime is —COCH$_2$ON=CHC(O)—; 'PEG' represents the formula —NH—(CH$_2$)$_3$—(OCH$_2$CH$_2$)$_3$—CH$_2$—NH—; and succ represents the formula —CO—(CH$_2$)$_2$—CO—.

55. A branched water-soluble polyamide comprising the formula:

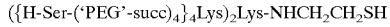
({H-Ser-('PEG'-succ)$_4$}$_4$Lys)$_2$Lys-NHCH$_2$CH$_2$SH wherein 'PEG' represents the formula —NH—(CH$_2$)$_3$—(OCH$_2$CH$_2$)$_3$—CH$_2$—NH—; and succ represents the formula —CO—(CH$_2$)$_2$—CO—.

56. A branched water-soluble polyamide comprising the formula:

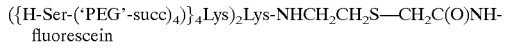
({H-Ser-('PEG'-succ)$_4$)}$_4$Lys)$_2$Lys-NHCH$_2$CH$_2$S—CH$_2$C(O)NH-fluorescein wherein 'PEG' represents the formula —NH—(CH$_2$)$_3$—(OCH$_2$CH$_2$)$_3$—CH$_2$—NH—; and succ represents the formula —CO—(CH$_2$)$_2$—CO—.

57. A branched water-soluble polyamide comprising the formula:

({peptide-('PEG'-succ)$_8$-Lys(oxime)amide}$_4$Lys)$_2$Lys-NHCH$_2$CH$_2$S—CH$_2$C(O)NH-fluorescein wherein said peptide comprises the sequence -ADGACRNPWC-(SEQ ID NO:6); oxime is —COCH$_2$ON=CHC(O)—; 'PEG' represents the formula —NH—(CH$_2$)$_3$—(OCH$_2$CH$_2$)$_3$—CH$_2$—NH—; and succ represents the formula —CO—(CH$_2$)$_2$—CO—.

58. A modified target molecule covalently attached through a multivalent linker to a homogenous branched water-soluble polyamide comprising two or more water-soluble polyamide chains of precise length, said chains having a polyethylene glycol-based repeating monomer unit and a terminal end group comprising a residue of a moiety selected from the group consisting of a target molecule, a multivalent linker, a terminal group, a reporter group, a protecting group, and a reactive group.

59. A branched water-soluble polyamide comprising two or more water-soluble polyamide chains of precise length covalently attached through a multivalent linker to a residue of a moiety selected from the group consisting of a target molecule, a terminal group attached to a support, a protecting group, and a reactive group, wherein said water-soluble polyamide chains of precise length are homogenous and comprise a polyethylene glycol-based repeating monomer unit and a terminal end group comprising a residue of a moiety selected from the group consisting of a target molecule, a linker, a terminal group, a reporter group, a protecting group and a reactive group.

60. A method of producing a composition comprising a branched water-soluble organic polyamide-based chain having a precise number of repeating units, said method comprising:

(a) forming a conjugate by reacting a multivalent linker with a homogenous water-soluble organic polyamide-based chain having a precise number of repeating units, wherein said multivalent linker comprises as components: (i) two or more first reactive groups capable of conjugation to a complementary reactive group; and (ii) a moiety selected from the group consisting of a target molecule, a terminal group attached to a support, a protecting group, and a second reactive group that is non-reactive with said complementary reactive group; and wherein said polyamide-based chain comprises as components: (i) a single complementary reactive group capable of conjugation to said two or more first reactive groups of said multivalent linker; and (ii) a repeat unit of the formula:

—{NH—Y—NH—CO—X—CO}$_n$— wherein X and Y are divalent organic radicals lacking reactive functional groups or are absent and are the same or different, and can vary independently with each of said repeating units; n is an integer from 2 to 100; and wherein a sufficient number of said repeating units comprise a water-soluble repeat unit to render said polyamide-based chain water soluble; and (b) isolating said conjugate, whereby said branched water-soluble polyamide composition is produced.

61. A method of producing a composition comprising a water-soluble organic polyamide-based chain of precise length having a precise number of repeating units, said method comprising:

(a) acylating amino groups of a compound of the formula:

(H—{NH—Y—NH—CO—X—CO}$_n$—{NH—Y'—NH}$_{n'}$)$_q$—V wherein X, Y and Y' are divalent organic radicals lacking reactive functional groups or are absent and are the same or different, and can vary independently with each repeating unit; n is an integer from 1 to 49; n' is 0 or 1; q is an integer from 1 to 10; V is a terminal group having a multivalent linker of the formula —Z—Q-support, wherein Z is a divalent linker or spacer or may be absent, Q is a linker or target molecule, and the support is a solid phase, matrix or surface, said acylating being performed with a molar excess of an activated form of a diacid derivative having the formula HOOC—X—COOH;

(b) activating carboxylate groups of the product of step (a);

(c) aminolysing the product of step (b) with a molar excess of a diamine having the formula NH$_2$—Y—NH$_2$;

(d) optionally, repeating steps (a)–(c) n more times, wherein any of the X and Y substituents of steps (a)–(d) may be the same or different from the X and Y substituents used in any previous said acylating and aminolysing steps, and wherein a sufficient number of said repeating units comprise a water-soluble repeat unit to render said polyamide-based chain water soluble; and (e) optionally, performing one or more additional coupling steps to extend the polyamide-based chain of the product of step (c) or (d) to generate a compound comprising the formula:

(U—{NH—Y—NH—CO—X—CO}$_n$—{NH—Y'—NH}$_{n'}$)$_q$—V wherein U is selected from the group consisting of a target molecule, a terminal group, a protecting group, and a reactive group.

62. The method of claim 61, wherein Q is a linker containing a cleavable moiety or a target molecule bound to the support by a linker containing a cleavable moiety, said method further comprising: cleaving said cleavable moiety to release a compound comprising said water-soluble organic polyamide-based chain of precise length from said support.

63. The method of claim 63, said method further comprising isolating said compound comprising said water-soluble organic polyamide-based chain of precise length.

64. The method of claim 63, wherein said isolated compound is homogenous.

65. An isolated homogenous water-soluble organic polyamide-based chain having a precise number of repeating units produced according to the method of claim 64.

66. A branched water-soluble polyamide composition comprising two or more water-soluble organic polyamide-based chains having a precise number of repeating units, wherein:

said repeating units are polyethylene glycol-based monomer units that comprise a divalent organic radical of the formula —a—(OCH$_2$CH$_2$)$_p$—b—, where a and b are divalent organic radicals lacking reactive functional groups that may be the same or different, and present or absent, and where p is an integer selected from the group consisting of 1–5; and said water-soluble organic polyamide-based chains have a repeat unit of the formula:

—{NH—Y—NH—CO—X—CO}$_n$— wherein X and Y are divalent organic radicals lacking reactive functional groups or are absent, and can be the same or different, and can vary independently with each of said repeating units; n is an integer from 2 to 100; and wherein said water-soluble organic polyamide-based chains contain a sufficient number of water-soluble repeat units to render said composition water-soluble; and said polyamide-based chains are covalently attached through a multivalent linker to a moiety selected from the group consisting of a target molecule, a terminal group, a protecting group, and a reactive group.

67. A branched water-soluble polyamide composition comprising two or more water-soluble organic polyamide-based chains having a precise number of repeating units, wherein:

said repeating units are polyethylene glycol-based monomer units that comprise a divalent organic radical of the formula —a—(OCH$_2$CH$_2$)$_p$—b—, where a and b are divalent organic radicals lacking reactive functional groups that may be the same or different, and present or absent, and where p is an integer that is small enough for the monomer unit to have a discrete value of p rather than a range;

said water-soluble organic polyamide-based chains have a repeat unit of the formula;

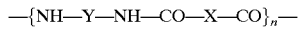
—{NH—Y—NH—CO—X—CO}$_n$— wherein X and Y are divalent organic radicals selected from the group consisting of —((CH$_2$)$_3$—(OCH$_2$CH$_2$)$_3$—CH$_2$)— and —((CH$_2$)$_3$—O—(CH$_2$)$_2$—(CH$_2$)$_2$—O—(CH$_2$)$_3$)— or are absent, and can be the same or different, and can vary independently with each of said repeating units; n is an integer from 2 to 100; and wherein said water-soluble organic polyamide-based chains contain a sufficient number of water-soluble repeat units to render said composition water-soluble; and said polyamide-based chains are covalently attached through a multivalent linker to a moiety selected from the group consisting of a target molecule, a terminal group, a protecting group, and a reactive group.

68. The branched water-soluble polyamide composition of claim 1, wherein said target molecule comprises an organic molecule having a molecular weight of between at least 100 and 10,000 Daltons.

* * * * *

UNITED STATES PATENT AND TRADEMARK OFFICE
CERTIFICATE OF CORRECTION

PATENT NO. : 6,552,167 B1
DATED : April 22, 2003
INVENTOR(S) : Keith Rose

It is certified that error appears in the above-identified patent and that said Letters Patent is hereby corrected as shown below:

<u>Column 47,</u>
Line 15, corresponding to the second line of Claim 41, insert the term -- V -- after the word "wherein" so as to cause column 47, line 15 to read as follows:
-- of claim 39, wherein V is selected from the group consisting --

Signed and Sealed this

Second Day of March, 2004

JON W. DUDAS
*Acting Director of the United States Patent and Trademark Office*

SEQUENCE LISTING

<160> NUMBER OF SEQ ID NOS: 6

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: synthetic

<400> SEQUENCE: 1

Gly Gly Leu Tyr Ala Cys His Met Gly Pro Met Thr Trp Val Cys Gln
 1               5                  10                  15

Pro Leu Arg Gly
            20

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: synthetic

```
<400> SEQUENCE: 2

Ser Val Trp Arg Trp Leu Pro Tyr Asp Lys Tyr
  1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 3

Ser Val Trp Arg Trp Leu Pro Tyr Asp Lys Tyr Glu
  1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: synthetic

<400> SEQUENCE: 4

Ser Val Trp Arg Trp Leu Pro Tyr Asp Lys Tyr Glu Lys
  1               5                  10

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: synthetic

<400> SEQUENCE: 5

Pro Gln Pro Gln Pro Lys Pro Gln Pro Gln Pro Gln Pro Gln Pro Lys
  1               5                  10                  15

Pro Gln Pro Lys Pro Glu Pro Glu
                 20

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: synthetic

<400> SEQUENCE: 6

Ala Asp Gly Ala Cys Arg Asn Pro Trp Cys
  1               5                  10
```